United States Patent
Ritterband et al.

(10) Patent No.: US 9,307,820 B2
(45) Date of Patent: Apr. 12, 2016

(54) TREATING LICE WITH GASEOUS COMPOUNDS IN AN AIRTIGHT SPACE

(75) Inventors: Menachem Ritterband, Ness Ziona (IL); Yinon Shlomi, Rehovot (IL)

(73) Assignee: NOVOMIC LTD., Moshav Mashen (IL)

( * ) Notice: Subject to any disclaimer, the term of this patent is extended or adjusted under 35 U.S.C. 154(b) by 527 days.

(21) Appl. No.: 13/544,269

(22) Filed: Jul. 9, 2012

(65) Prior Publication Data

US 2012/0272991 A1 Nov. 1, 2012

Related U.S. Application Data

(63) Continuation-in-part of application No. 12/901,544, filed on Oct. 10, 2010, now abandoned, which is a continuation-in-part of application No. 12/473,058, filed on May 27, 2009, now abandoned, which is a continuation-in-part of application No. PCT/IL2008/000031, filed on Jan. 6, 2008.

(60) Provisional application No. 60/878,351, filed on Jan. 4, 2007.

(51) Int. Cl.
| | |
|---|---|
| *A01M 13/00* | (2006.01) |
| *A45D 19/14* | (2006.01) |
| *A45D 19/16* | (2006.01) |
| *A01N 37/02* | (2006.01) |
| *A45D 19/00* | (2006.01) |

(52) U.S. Cl.
CPC ............... *A45D 19/14* (2013.01); *A01N 37/02* (2013.01); *A45D 19/16* (2013.01); *A45D 2019/0033* (2013.01); *A45D 2019/0041* (2013.01)

(58) Field of Classification Search
CPC .. A01M 1/2022; A01M 13/00; A01M 13/003
USPC ........... 43/132.1, 125, 129, 1, 124; 222/5, 80, 222/81, 85, 86, 89, 90
IPC ............................................. A01M 13/00, 1/20
See application file for complete search history.

(56) References Cited

U.S. PATENT DOCUMENTS

| | | | |
|---|---|---|---|
| 2,033,357 A | | 3/1936 | Riker et al. |
| 3,885,742 A | * | 5/1975 | Menzel .......................... 239/272 |

(Continued)

FOREIGN PATENT DOCUMENTS

| | | | | |
|---|---|---|---|---|
| DK | WO 2008071193 A1 | * | 6/2008 | ............. A45D 20/22 |
| EP | 0221004 A2 | | 5/1987 | |

(Continued)

OTHER PUBLICATIONS

Office Action of U.S. Appl. No. 12/901,544 mailed on Jun. 15, 2012.

*Primary Examiner* — Lisa Tsang
(74) *Attorney, Agent, or Firm* — Mark M. Friedman

(57) ABSTRACT

A system and a method to treat lice and nits on a head of a patient. The system includes a cap for defining an airtight space around the head and a container for storing a mixture of gases for treating lice, a gas release mechanism for delivering the mixture of gases into the airtight space as an aerosol, and a gas distribution device having plurality of gas delivery pins. The mixture of gases causes irreversible damage to essential mechanisms of the lice. According to another embodiment of the present invention the system includes a cap for defining an airtight space around the head and an active agent container. The active agent of the type of acetic acid, stored in a liquid state, and vaporized during use, then circulated toward the cap.

7 Claims, 16 Drawing Sheets

(56) References Cited

U.S. PATENT DOCUMENTS

| | | | |
|---|---|---|---|
| 4,228,124 A * | 10/1980 | Kashihara | A01M 1/2072 392/386 |
| 4,947,578 A | 8/1990 | Anderson et al. | |
| 4,966,755 A * | 10/1990 | Smith | A01M 13/00 239/136 |
| 4,995,555 A * | 2/1991 | Woodruff | 239/43 |
| 5,074,439 A * | 12/1991 | Wilcox | A01M 31/008 206/38 |
| 5,205,067 A * | 4/1993 | Thomas | 43/125 |
| 5,694,990 A * | 12/1997 | Crima | 141/330 |
| 5,839,221 A * | 11/1998 | Ron et al. | 43/132.1 |
| 6,553,712 B1 * | 4/2003 | Majerowski et al. | 43/131 |
| 6,691,335 B1 | 2/2004 | Keith | |
| 7,028,348 B2 | 4/2006 | Tadake et al. | |
| 7,922,984 B2 | 4/2011 | Hamilton et al. | |
| 8,146,607 B2 | 4/2012 | Rabin et al. | |
| 2005/0112163 A1 | 5/2005 | Nishimura et al. | |
| 2006/0091570 A1 | 5/2006 | Reece | |
| 2009/0032049 A1 * | 2/2009 | Rabin et al. | 132/270 |
| 2009/0235949 A1 | 9/2009 | Ritterband et al. | |
| 2009/0260276 A1 | 10/2009 | Kirsch et al. | |

FOREIGN PATENT DOCUMENTS

| | | | |
|---|---|---|---|
| EP | 2255778 | 12/2010 | |
| GB | 2347082 A * | 8/2000 | A61K 31/19 |
| WO | WO 00/01347 | 1/2000 | |
| WO | WO 00/57704 | 10/2000 | |
| WO | WO 03/045145 * | 6/2003 | |
| WO | WO 2007/056813 | 5/2007 | |
| WO | WO 2008081462 | 7/2008 | |

* cited by examiner

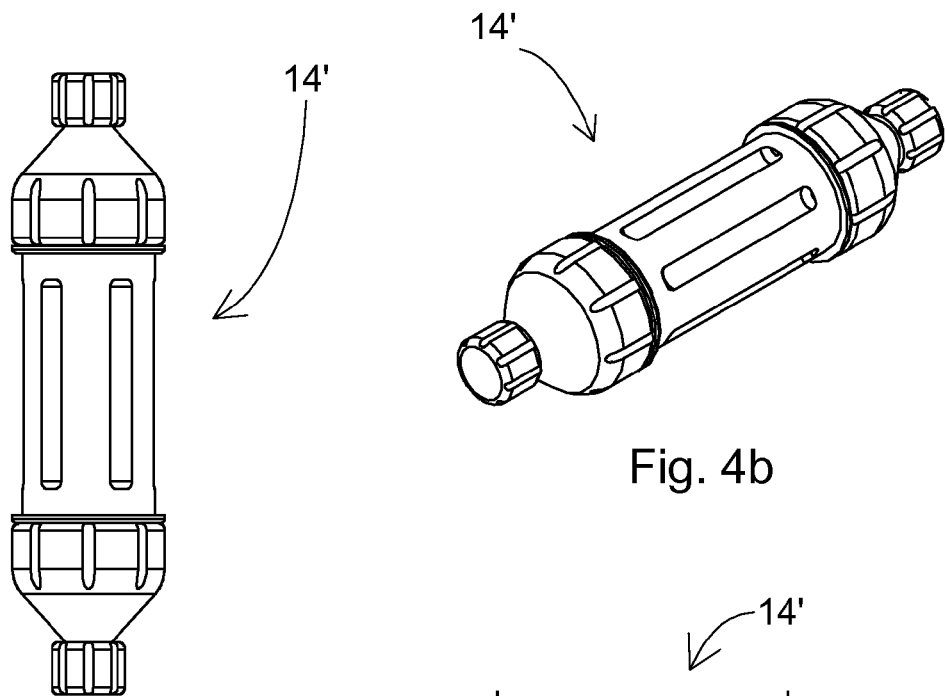
Fig. 4b
Fig. 4a
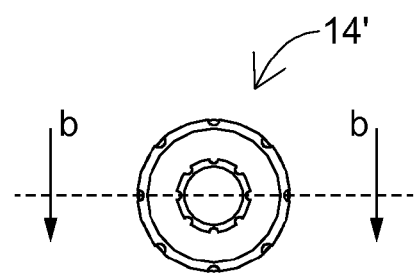
Fig. 4c
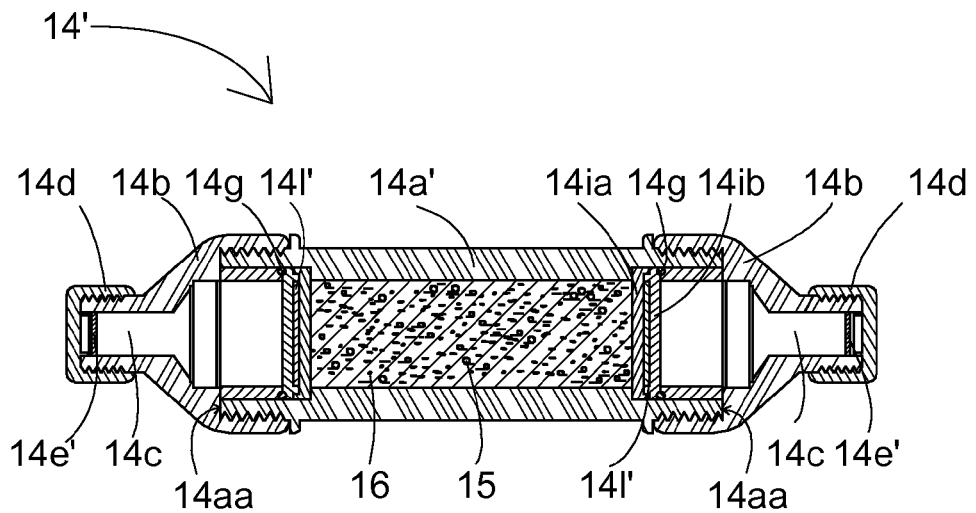
Fig. 4d

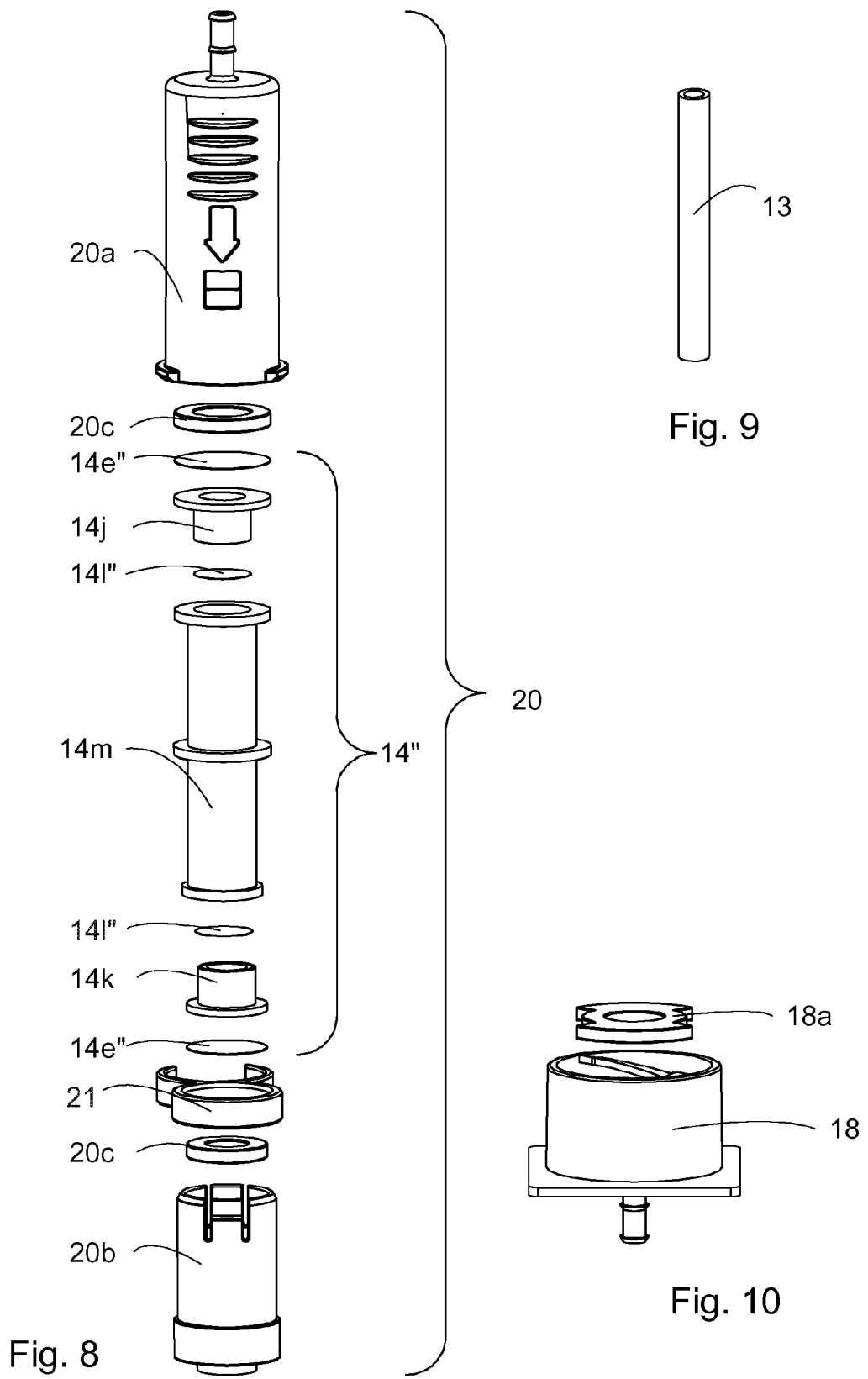

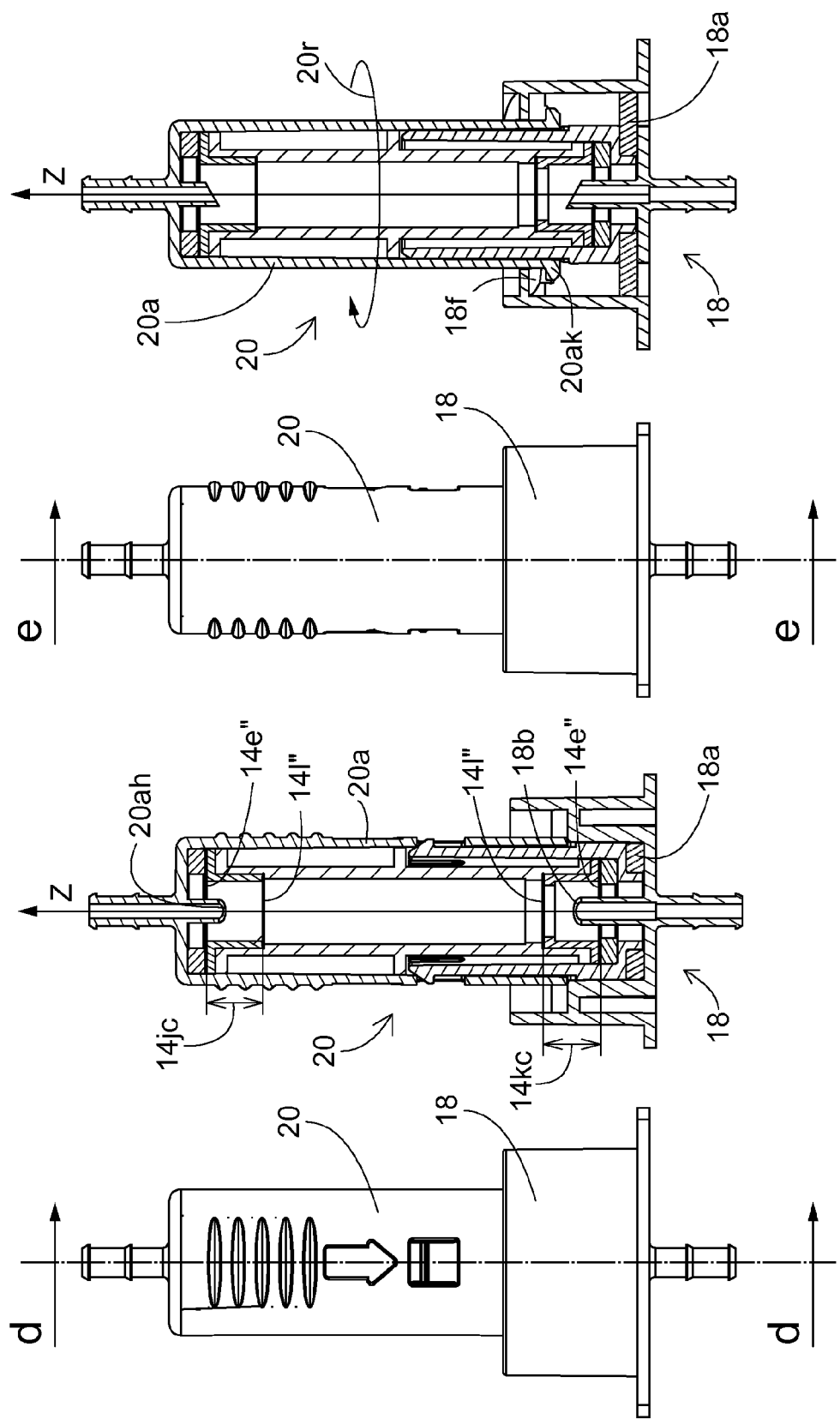

TREATING LICE WITH GASEOUS COMPOUNDS IN AN AIRTIGHT SPACE

CROSS-REFERENCE TO RELATED APPLICATIONS

This application is a continuation-in-part of U.S. patent application Ser. No. 12/901,544 filed on Oct. 10, 2010 now abandoned which is a continuation-in-part of U.S. patent application Ser. No. 12/473,058 filed on May 27, 2009 now abandoned which is a continuation-in-part of International Patent Application No. PCT/IL2008/000031 filed Jan. 6, 2008, which claims priority benefits from U.S. Provisional Patent Application No. 60/878,351, filed on Jan. 4, 2007, all of which are incorporated by reference in their entireties.

FIELD OF THE INVENTION

The present invention relates to the field of medical treatment systems, more particularly, to a system and method for treating an infestation of head lice.

BACKGROUND OF THE INVENTION

Infestation of the human body by lice is an increasingly prevalent social and health problem in many countries in the world. Lice infest hundreds of millions of people each year. Lice are very small insects, about 2-3 mm in length. They deposit eggs either on a hair or fabric fiber and attach them firmly with a cement-like excretion.

The life cycle of lice comprises an egg stage, three nymphal stages, and an adult stage, and takes about one month. A female louse lays approximately 100 eggs, which are glued to hairs of the host. The eggs generally hatch in about six to ten days, depending on temperature. The nymphs, (the larval stage in insect development), and adults suck blood, causing disturbance (itching, also known as pruritus) and secondary infection. The empty shells remaining after the nymphs emerge from the eggs look like white grains of sand.

Lice, being insects, use tracheae for respiration. Tracheae are a system of internal tubes (invaginations of the cuticle) penetrating the insect's body, through which air diffuses or is being pumped directly to the body tissues. Within body cells, chemical respiration takes place in the mitochondria, where ATP is produced under oxygen consumption.

The common treatment methods against lice involve liquids or lotions.

An apparatus and process for killing human and animal vermin, which discloses treatment of lice within a gas-tight garment by using a volatile liquid, specifically methyl-formate, that is spread on a pad inside the garment and evaporates inside the garment, is described in U.S. Pat. No. 2,033,357 of Riker et al. patented 1936.

A method and device for eradicating lice and nits form an infested area, particularly the scalp of a human being, comprises a plastic or rubber cap for covering the head of a human being, and means for filling the cap with an inner gas, such as carbon dioxide from a pressurized-gas cartridge, in order to suffocate the lice and the nits enclosed by the cap, is described in European Patent Application No. 86630160.9, publication No. EP0221004, of Scolnik et al. filed Oct. 30, 1986.

A formulation for controlling human lice, which discloses pediculicidal formulations comprising a spinosyn, or a physiologically acceptable derivative or salt thereof, and a physiologically acceptable carrier, and methods of controlling lice infestations in a human with these formulations are provided in International Patent Application No. PCT/US1999/013925, publication No. WO/2000/001347, of Snyder, filed Jun. 21, 1999.

A pediculicide composition, in particular, a composition comprising a sesquiterpene alcohol and a suitable carrier, is described in International Patent Application No. PCT/AU2006/001720, publication No. WO/2007/056813, of Found, filed Nov. 17, 2006.

A method and composition for controlling lice on an organism is described in International Patent Application No. PCT/NL2000/000196, publication No. WO/2000/057704, of Kussendrager et al. filed Mar. 23, 2000.

All of these applications are incorporated by reference for all purposes as if fully set forth herein.

Although the various breeds of human lice are related, each of them has specific characteristics with regard to habitat and feeding. For example, head lice are small hard-shelled ectoparasites which cling to hair shafts while feeding, mating and laying eggs. The louse must remain on the head or it will die within a short period of time. Head lice proliferate at an incredible rate. A louse is ready to mate and reproduce within 10 hours after hatching. Under ideal conditions, a female louse may produce up to 300 eggs in its lifetime. Ideal conditions include an adequate food supply, environmental temperatures from about 28° C. to about 32° C., and relative humidity of about 70% to about 90%.

The louse's hard chitinous exoskeleton serves as protection from external elements. Lice eggs (or ova) are similarly protected by a chitinous sheath surrounding the eggs and attached to the hair shaft. Although lice may be affected by the use of an insecticide, the eggs often remain resistant to attack. Thus, present art optimum treatment of a lice infestation includes both a pediculicide, which kills the adult lice, and an ovicide, which interrupts the development of the eggs.

Treatment for eliminating head lice traditionally included home remedies such as smearing mayonnaise, olive oil, hair pomade, or some other heavily viscous material about an infested scalp coupled with rigorous combing of the hair and meticulous removal of adult lice, nymphs, and nits. Though these home remedies do not kill head lice, the prevailing thought is that the viscosity of the material makes it hard for head lice to roam about the scalp, making for easy removal. Such home remedies are usually ineffective at controlling head lice due to the ability of the lice to revive rapidly once these materials are removed.

More effective treatments for eliminating head lice involve massaging the infested scalp with over-the-counter (OTC) topical creams containing active insecticides. Because of their potential toxicity to the human host, the use of these topical formulas is regulated by the FDA. Over-the-counter insecticides typically have pyrethrins or permethrin as active ingredients Biologically active agents have been used for some time in attempts to control lice. For example, lindane (gammabenzene hexachloride), organophosphates (malathion), natural pyrethrins, and synthetic compounds known as pyrethroids (such as permethrin) have been used as pediculicides in lice treatment formulations. These agents however, have drawbacks. Lindane has a poor safety profile, and lice have developed resistance to it. Natural pyrethrin requires frequent follow-up treatments because it provides only short term residual action. Synthetic pyrethroids, although more effective against lice than natural pediculicides, are often more toxic to the subject being treated.

Strains of head lice have been identified worldwide which are resistant to all currently available topical treatments. Possible neural damage to the human host prevents raising the insecticide levels above the current threshold in an attempt to combat these newer treatment resistant head lice.

A system for treating lice with gaseous compounds in an airtight space is described in European Patent Application No. 09163262.0 publication No. EP2255778, of Ritterband, Menachem and Shlomi, Yinon, which is incorporated by reference for all purposes as if fully set forth herein.

FIG. 1a of the prior art illustrates a system for treating lice and nits 1, on a head 10 of a patient, according to European Patent Application No. 09163262.0.

A container 14 is connected on both ends to connecting tubes 13. In this configuration, the container 14 contains active agent 15 in a gas state. The flow of the active agent 15 is achieved by releasing vaporizing and circulating gas 12 from within a vaporizing and circulating gas source 11. The releasing is enabled by opening a valve, for example by a gas source handle 11a.

FIG. 1b of the prior art shows a container 14, according to the European Patent Application No. 09163262.0.

The container 14 contains an immersed material 16, which is a sponge, immersed with active agent 15. In this configuration, an active agent 15, of acetic acid type is inserted into the container 14 and then evaporates.

This method of storage of the active agent 15 is insufficiently effective.

FIG. 2 of the prior art is a schematic block diagram of a system for treating lice and nits 1, according to the European Patent Application No. 09163262.0.

A vaporizing and circulating gas source 11 contains a vaporizing and circulating gas 12, which during activation flows through a connecting tube 13 to a container 14. Container 14 contains active agent 15 and immersed material 16, such as a sponge.

The vaporizing and circulating gas 12 vaporizes the active agent 15 and causes it to flow through a connecting tube 13 to a cap 17 for the purpose of performing the treatment of lice and nits.

None of the prior art provides a sufficiently effective solution, and there is therefore a need for a system and a method for treating an infestation of head lice.

SUMMARY OF THE INVENTION

The present invention teaches an effective solution for an infestation of head lice, including a system and method of use, which eliminates both the lice and their eggs by means of effective insertion of gas near the roots of the patient's hair, with the gas including toxic material or materials, and enabling a combined attack also including suffocating gases.

The system for treating lice and nits on a head of a patient includes a cap for defining an airtight space around the head and a container for storing active agent or a mixture of active agents for treating lice. In addition, a vaporizing and circulating gas source is also provided. Specifically, the mixture of active agents is selected so that it causes irreversible damage to at least one essential mechanism of said lice.

Experiments have shown that the carboxylic acids most effective for use according to the present invention are formic acid and acetic acid.

Formic acid, $CH_2O_2$, is the simplest carboxylic acid.

Acetic acid, $C_2H_4O_2$, also known as an organic acid, is a simple carboxylic acid too, which is a water-soluble component of vinegar, and has been used, in liquid, as a folk remedy which dissolves the cement of lice eggs.

According to the teaching of the present invention there is provided a A system for treating lice and nits (1) on a head of a patient, the system including: (A) a container (14) for storing a predetermined volume of active agent (15) and immersed material (16); (B) a vaporizing and circulating gas source (11) for storing vaporizing and circulating gas (12), operatively connected to the container (14); and (C) a cap (17) operatively connected to the container (14); characterized in that the container (14) is located within a capsule (20) wherein the capsule (20) includes: (a) an external cylinder (20a); (b) an internal cylinder (20b) partially located within the external cylinder (20a), and (c) a safety-catch mounted on the internal cylinder (20b) for preventing a linear movement (20l) of the external cylinder (20a) along a symmetry axis (Z); and wherein the container (14") including: (i) a container cylinder (14m) having a container main wall (14a"), a container first end (14sa), and a container second end (14sb), wherein at the container first end (14sa) the container main wall (14a") has a container first internal diameter (14qa), and wherein at the container second end (14sb) the container main wall (14a") has a container second internal diameter (14qb); (ii) a first carrier (14j) disposed on the container cylinder (14m) at the first end (14sa), partially located within the container cylinder (14m), wherein the first carrier (14j) includes: (ii-i) a first carrier cylinder (14ja) having a first carrier cylinder exterior diameter (14jd) wherein the first carrier cylinder exterior diameter (14jd) and the container first internal diameter (14qa) have substantially the same value; and (iii) a second carrier (14k) disposed on the container cylinder (14m) at the second end (14sb), partially located within the container cylinder (14m), wherein the second carrier (14k) including: (iii-i) a second carrier cylinder (14ka) having a second carrier cylinder exterior diameter (14kd) wherein the second carrier cylinder exterior diameter (14kd) and the container second internal diameter (14qb) have substantially the same value.

According to the teaching of the present invention there is provided a method for treating lice and nits on a head of a patient including the stages of: (a) mounting a cap (17) over the head of the patient; (b) connecting a container (14) to a vaporizing and circulating gas source (11) containing vaporizing and circulating gas (12); (c) delivering, a predetermined volume of active agent (15) for treatment of lice infestation wherein the active agent (15) contain acidic active ingredient component; (d) waiting at least a predetermined minimal duration time; and (e) removing the cap (17) from the head after the predetermined minimal duration time, characterized in that the stage of delivering a predetermined volume of active agent (15) for treatment of lice infestation including the sub-stages of: (i) holding external cylinder (20a) of capsule (20), with the capsule (20) containing a container (14"), which contains the active agent (15) and porous particles (16a) (sub-stage 92); (ii) removing a safety-catch (21) from an internal cylinder of the capsule 20 (sub-stage 93); (iii) partially inserting the internal cylinder (20b) into an adapter (18), which includes an adapter tube 18c (sub-stage 94); (iv) after a performing a linear movement of an external cylinder (20a), an external cylinder second end (20aj) is halted within the adapter (18), and continuing pressing of the external cylinder (20a) in linear movement toward the adapter (18) and rotating the external cylinder (20a), while adapter tracks (18f) apply forces to an external cylinder outer clips (20ak) until the linear and rotational movement between external cylinder (20a) and the adapter (18) are stopped and are locked together by forces of friction, as a result of a contact generated between the external cylinder outer clip (20ak) and adapter track stoppers (18g) (sub-stage 95); and (v) in the course of the linear movement of the external cylinder (20a) with regard to the internal cylinder (20b), perforating two sealing discs (14e") for enabling flow from and through the container (14") (substage 96).

Additional objects and advantages of the invention will be set forth in part in the description which follows and, in part, will be obvious from the description, or may be learned by practice of the invention.

BRIEF DESCRIPTION OF THE DRAWINGS

The invention is herein described, by way of example only, with reference to the accompanying drawings, wherein:

FIG. 4a is a side view schematic illustrations of a container of the first embodiment of the system for treating lice and nits, according to the present invention.

FIG. 4b is an isometric view schematic illustration of an active agent container of the first embodiment of the system for treating lice and nits, according to the present invention.

FIG. 4c is a top view schematic illustration of an active agent container of the first embodiment of the system for treating lice and nits, according to the present invention, upon which a section plane b-b is marked.

FIG. 4d is a cross sectional view b-b illustration of an active agent container of the first embodiment of the system for treating lice and nits, according to the present invention.

FIG. 8 is an exploded isometric view schematic illustration of a capsule and a safety-catch, according to the second embodiment of the present invention.

FIG. 9 is an isometric view schematic illustration of a connecting tube, according to the embodiments of the present invention.

FIG. 10 is an isometric view schematic illustration of an adapter and an adapter seal, according to the second embodiment of the present invention.

FIG. 15a is a side view schematic illustrations of a capsule, and an adapter, of the second embodiment of the system for treating lice and nits, engaged with each other, according to the present invention, upon which a section plane d-d is marked.

FIG. 15b is a cross sectional view d-d illustration of a capsule, and an adapter, of the second embodiment of the system for treating lice and nits, engaged with each other, according to the present invention.

FIG. 15c is a front view schematic illustration of, a capsule, and an adapter, of the second embodiment of the system for treating lice and nits, engaged with each other, according to the present invention, upon which a section plane e-e is marked.

FIG. 15d is a cross sectional view e-e illustration of a capsule, and an adapter, of the second embodiment of the system for treating lice and nits, engaged with each other, according to the present invention.

DETAILED DESCRIPTION OF EMBODIMENTS

Figure 1A:
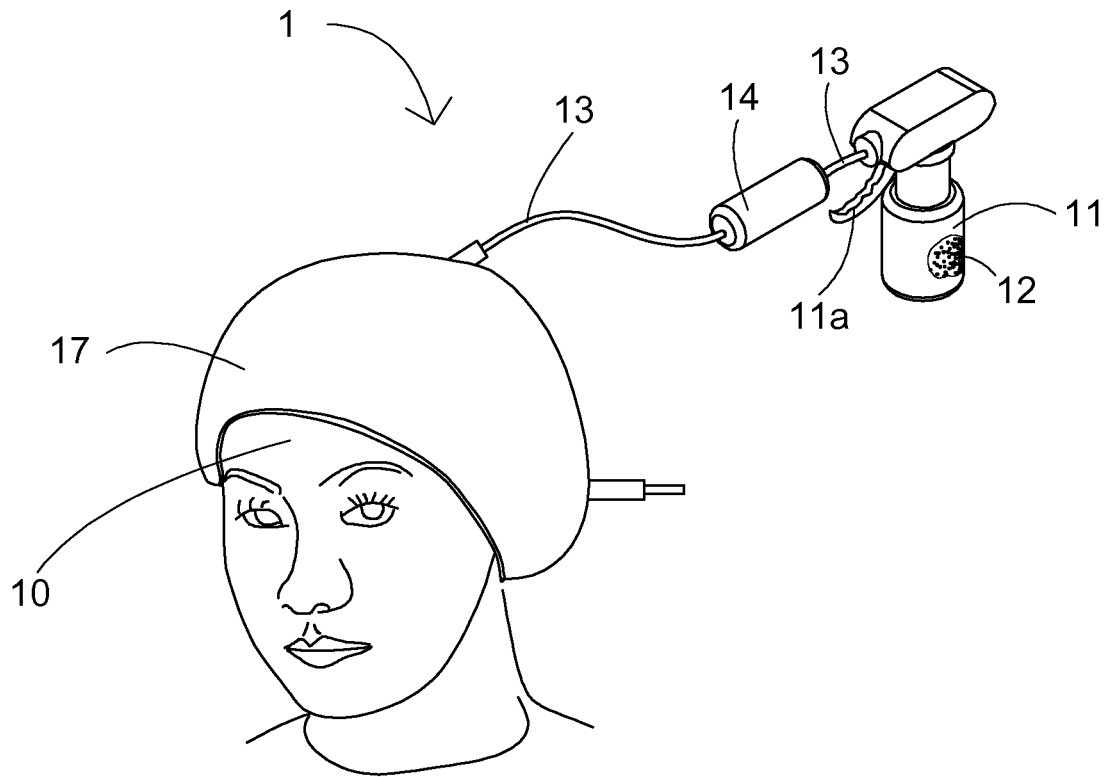
FIG. 1a of the prior art illustrates a system for treating lice and nits, on a head of a patient, according to European patent application No. 09163262.0.
Figure 1B:
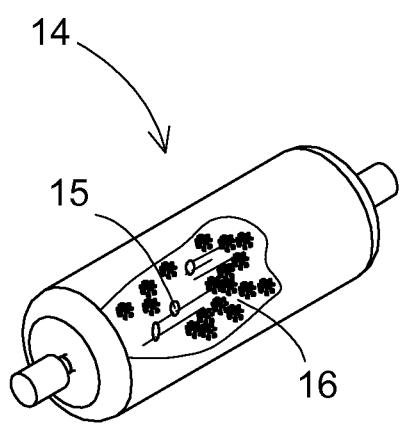
FIG. 1b of the prior art shows a container, according to the European patent application No. 09163262.0.
Figure 2:
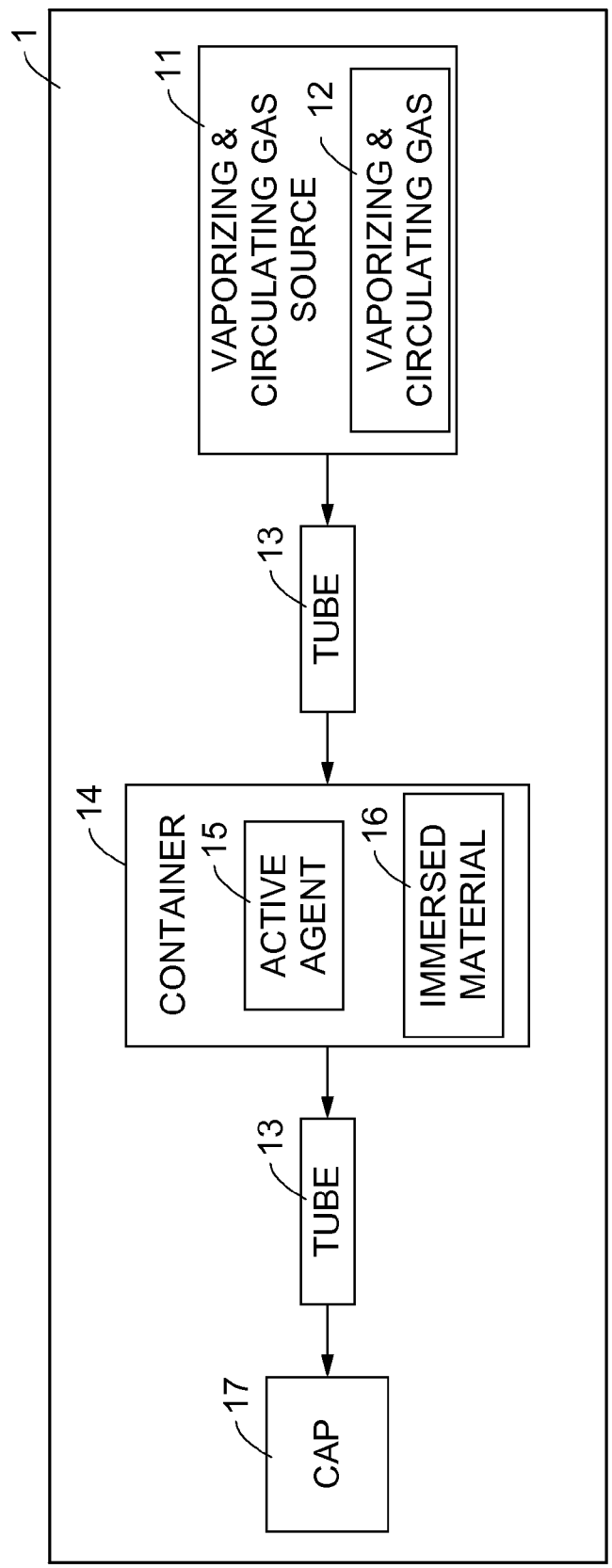
FIG. 2 of the prior art is a schematic block diagram of a system for treating lice and nits, according to the European patent application No. 09163262.0.

The present invention is of a system and a method for treating lice and nits on a head of a patient.

The principles and operation of a system and a method for treating lice and nits on a head of a patient, according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

The following list is a legend of the numbering of the application illustrations:

1 system for treating lice and nits
10 head
11 vaporizing and circulating gas source
11a gas source handle
12 vaporizing and circulating gas
13 connecting tube
13a connector
14 container
14a container main wall
14aa container main wall end
14b container end wall
14c fluid passage
14d lid
14e sealing disc
14g o-ring seal
14i filter compartment
14ia filter compartment first disc
14ib filter compartment second disc
14ic filter compartment disc hole
14j first carrier
14ja first carrier cylinder
14jb first carrier disc
14jc first carrier length
14jd first carrier cylinder exterior diameter
14je first carrier interior diameter
14jh first carrier ring disc exterior diameter
14k second carrier
14ka second carrier cylinder
14kb second carrier disc
14kc second carrier length
14kd second carrier cylinder exterior diameter
14ke second carrier interior diameter
14kf second carrier ring diameter
14kg second carrier ring
14kh second carrier ring disc exterior diameter
14l filter
14m container cylinder
14na container main wall first thickness
14nb container main wall second thickness
14nc container main wall third thickness
14oa container first outer ring
14oad container first outer ring diameter
14ob container second outer ring
14obd container second outer ring diameter
14oc container third outer ring
14ocd container third outer ring diameter
14od container interior ring
14pa container first stair depth
14pb container second stair depth
14qa container first internal diameter
14qb container second internal diameter
14ra container first internal stair
14rb container second internal stair
14rc container third internal stair
14sa container first end
14sb container second end
15 active agent
16 immersed material
16a porous particle
16aa pores
16ab pore opening
16ac opening diameter
16ad porous particle size
16ae porous particle surface
16p surface point
17 cap (airtight)
17a distributor
17b injection tube
17c interior side of the cap
17d injection tube stitch
17e injection tube edge
17f flow opening
18 adapter
18a adapter seal 18*aa* adapter seal body
18*ab* adapter seal niches
18*ac* adapter seal hole
18*b* adapter piercer
18*c* adapter tube
18*d* adapter outer cylinder
18*da* adapter outer cylinder inner face
18*e* adapter base
18*f* adapter track
18*g* adapter track stopper
18*h* adapter inner cylinder segment
18*i* adapter base opening segment
18*j* adapter inner space
18*k* adapter track inner cylinder segment gap
18*l* adapter track free end
18*m* adapter inner stair
20 capsule
20*a* external cylinder
20*aa* external cylinder wall
20*ab* external cylinder window
20*ac* gripping means
20*ad* arrow mark
20*ae* external cylinder first end
20*af* external cylinder end wall
20*ag* external cylinder tube
20*ah* external cylinder piercer
20*ai* external cylinder tube internal length
20*aj* external cylinder second end
20*ak* external cylinder outer clip
20*al* external cylinder wall internal diameter
20*b* internal cylinder
20*ba* internal cylinder wall
20*bb* internal cylinder hook
20*bba* internal cylinder hook head
20*bc* internal cylinder slot
20*bd* internal cylinder outer ring
20*be* internal cylinder base
20*bf* internal cylinder base ring
20*bg* internal cylinder wall internal diameter
20*bh* internal cylinder wall exterior diameter
20*bi* internal cylinder base ring exterior diameter
20*bj* internal cylinder outer ring outer diameter
20*bk* internal cylinder first end
20*bl* internal cylinder second end
20*bm* internal cylinder outer_stair
20*c* sealing ring
20*l* (external cylinder) linear movement (direction)
20*r* external cylinder rotational direction
21 safety-catch
21*a* safety-catch handle
21*b* safety-catch stopper arm
21*c* safety-catch stopper arm width
21*d* external cylinder movement range
Alfa adapter track segment angle
81-86 a method of treating lice and nits on a head of patient stages Note: when the association of a reference number to a specific one of the two embodiments of the present invention needs to be distinguished, the reference number associated to the first embodiment will be marked with a single apostrophe, and the reference number associated to the second embodiment will be marked with a double apostrophe, for example: system for treating lice and nits 1', (in accordance with the first embodiment of the present invention), and system for treating lice and nits 1", (in accordance with the second embodiment of the present invention).

The disclosed invention describes a system and method for treating lice on a patient's head. The invention utilizes a cap for defining the space around the treated hair, and an airtight sealing of the space around the treated hair, to apply an active agent for treating lice. Reducing the volume that is treated allows using a small amount of active agent, such that in case of releasing the active agent outside the cap, the patient faces no danger due to the strong dilution of the active agent. Keeping the active agent compressed in a container enables a rapid delivery of the active agent into the airtight space.

This specification is not intended in any way to limit the present invention to any specific method of applying pressure to the material in order to deliver it in gas form.

Figure 3A:
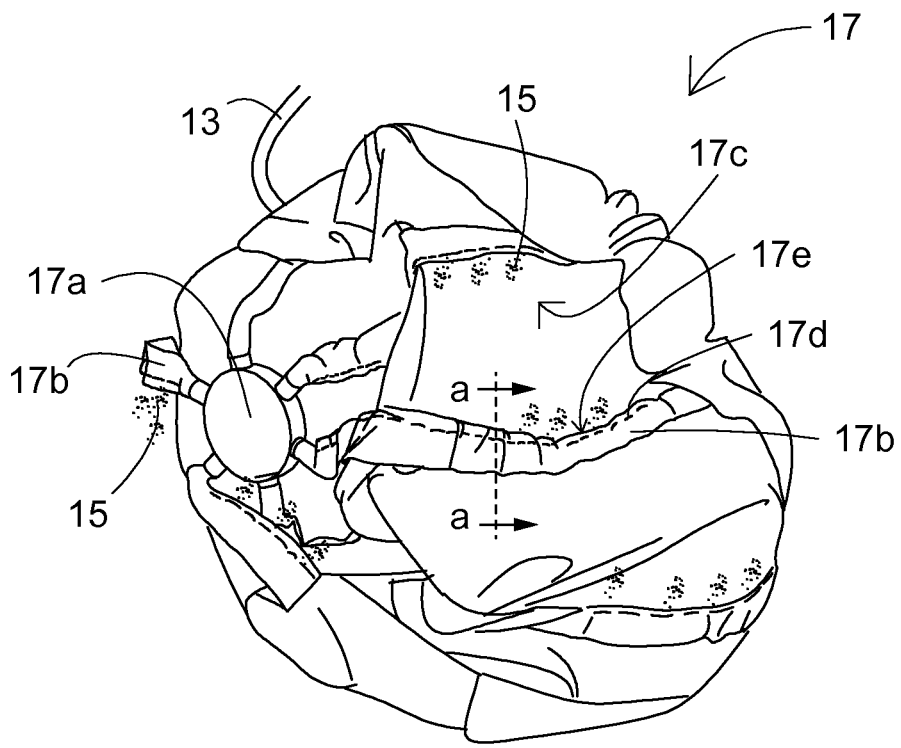
FIG. 3a illustrates a cap of a first embodiment of a system for treating lice and nits, according to the present invention, upon which a section plane a-a is marked.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 3*a* illustrates a cap 17 of a first embodiment of a system for treating lice and nits 1', (not fully shown in the present drawing), according to the present invention, upon which a section plane a-a is marked.

Cap 17 is shown in the present illustration from its inside, with its central part pulled and diverted toward the left side of the illustration, and being equipped with a distributor 17*a*. During treatment, the distributor 17*a* receives a supply of active agent 15 at a higher pressure than that of the environment.

The active agent 15 comes through the connecting tube 13 and the distributor 17*a* disperses its circulation to several injection tubes 17*b*. The injection tubes 17*b* are attached to the interior side of the cap 17*c*. An injection tube 17*b* includes openings through which the active agent 15 flows.

Figure 3B:
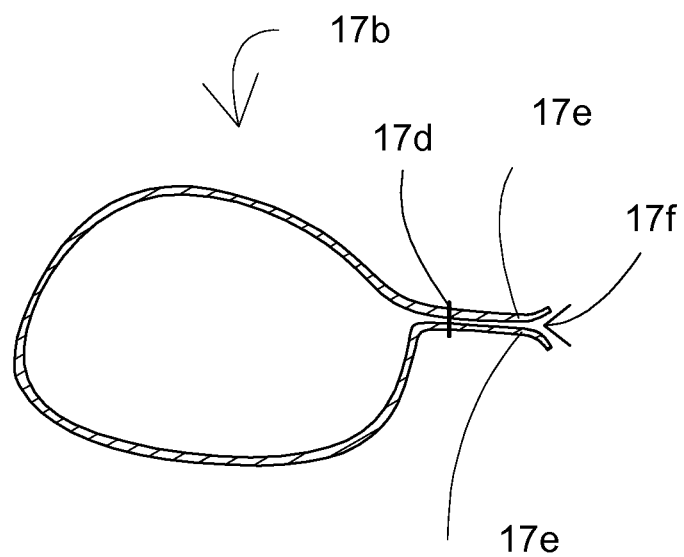
FIG. 3b is a cross sectional view a-a illustration of an injection tube, of the cap of the first embodiment of the system for treating lice and nits, according to the present invention.

FIG. 3*b* is a cross sectional view a-a illustration of an injection tube 17*b*, of the cap 17 of the first embodiment of the system for treating lice and nits 1', according to the present invention.

The injection tube 17*b* can be composed of a thin material, relative to its lateral section, for example fabric, folded double lengthwise. Along the injection tube edges 17*e* are injection tube stitches 17*d*, which connect these edges however do not seal them, and comprise a flow opening 17*f*.

FIG. 4*a* is a side view schematic illustrations of a container 14' of the first embodiment of the system for treating lice and nits 1', according to the present invention.

FIG. 4*b* is an isometric view schematic illustration of an active agent container 14' of the first embodiment of the system for treating lice and nits 1', according to the present invention.

FIG. 4*c* is a top view schematic illustration of an active agent container 14' of the first embodiment of the system for treating lice and nits 1', according to the present invention, upon which a section plane b-b is marked.

FIG. 4*d* is a cross sectional view b-b illustration of an active agent container 14' of the first embodiment of the system for treating lice and nits 1', according to the present invention.

The present illustration shows the container 14', in storage state, when it is inactive, and contains immersed material 16 and active agent 15 in a liquid state, absorbed within the immersed material 16. The immersed material 16 can be a sponge in a single lump, several smaller lumps, or a large number of unbound small crumb-size pieces, spherical or of another shape, including amorphous pieces, or porous particles. The pieces of the immersed material 16 improve the evaporation.

The container 14' can be designated for single-time use.

A particularly effective form of the active agent 15 for this specific purpose is acetic acid ($CH_3COOH$).

A sufficient quantity of acetic acid for one treatment, stored in container 14', can be in the range of 1 to 5 cubic milliliters.

During circulation of the vaporizing and circulating gas source 11, (not shown in the present illustration), the liquid part of the active agent 15, if there is part of it in a liquid state, evaporates, and only its vapors emerge and flow from the container 14'.

The container 14' includes a container main wall 14a', whose shape can be as of a cylindrical tube wall, with a circular section, having at each of its ends, the container main wall end 14aa, a container end wall 14b, the shape of each can include a conical segment, which tapers and becomes narrower in the outward direction, having a circular section, which extends into a segment resembling a cylindrical tube wall, with a circular section, creating at it center a fluid passage 14c.

One fluid passage 14c serves as an inlet, while the other serves as an outlet.

In storage state, the container 14' is closed on both ends by lids 14d which are removed from their places prior to use. Near the end of each fluid passage 14c, a sealing disc 14e' can be placed to prevent any leakage of active agent 15 during storage.

Figure 5:
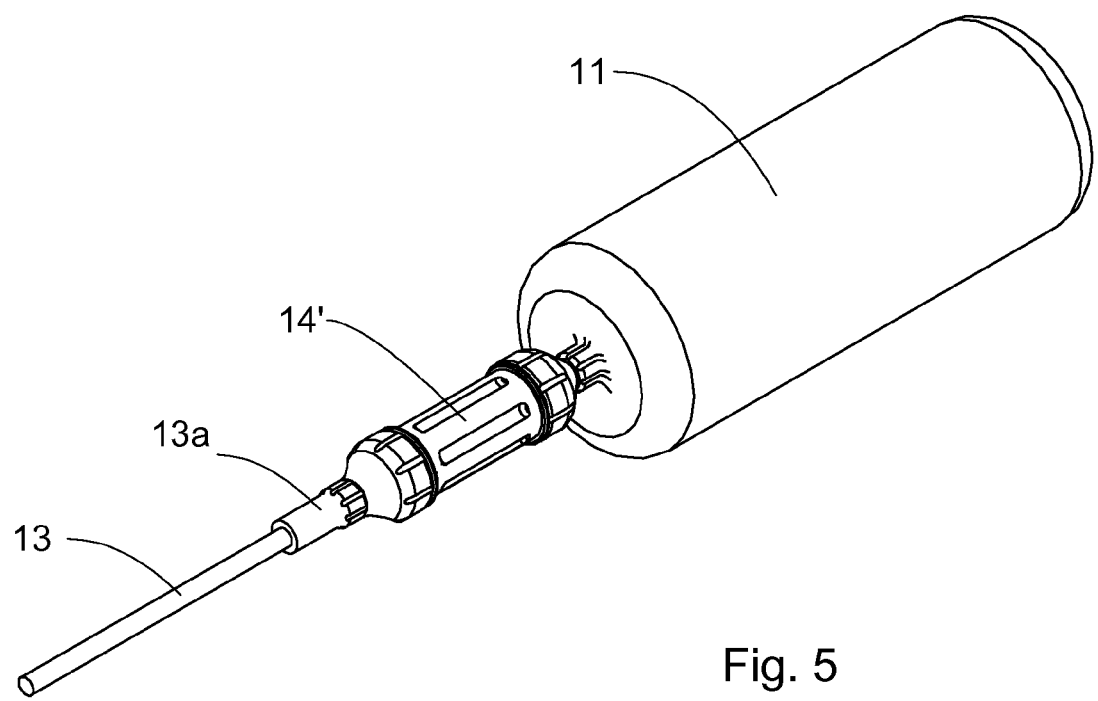
FIG. 5 is an isometric view schematic illustration of a vaporizing and circulating gas source, a container, a connector and a connecting tube, of the first embodiment of the system for treating lice and nits, according the present invention.

The sealing discs 14e' are broken during preparation for use, for example during assembly of a connector 13a, (not shown in the present illustration, shown in FIG. 5).

Furthermore, the container 14' can include two o-ring seals 14g and two filters 14l'.

Figure 4E:
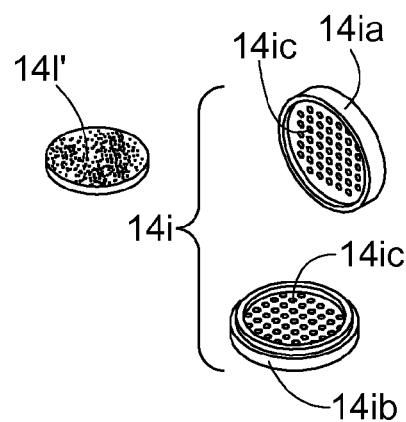
FIG. 4e is an isometric view schematic illustration of filter compartment and a filter, of the container, of the system for treating lice and nits 1, according to the first embodiment of the present invention.

FIG. 4e is an isometric view schematic illustration of filter compartment 14i and a filter 14l', of the container 14', (not shown in the present drawing), of the system for treating lice and nits 1', according to the first embodiment of the present invention.

The present illustration shows one possible configuration for installing the filter 14l' in its place, including a filter compartment 14i composed of two parts, a filter compartment first disc 14ia, and a filter compartment second disc 14ib each of which has filter compartment disc holes 14ic, with the filter 14l' disposed between them.

FIG. 5 is an isometric view schematic illustration of a vaporizing and circulating gas source 11, a container 14', a connector 13a and a connecting tube 13, of the first embodiment of the system for treating lice and nits 1', according the present invention.

The present illustration presents a vaporizing and circulating gas source 11 which is connected directly to the container 14'. Likewise, the connecting tube 13 is also connected to the container 14', a connection made, in the case of the present illustration, by means of connector 13a.

Figure 6A:
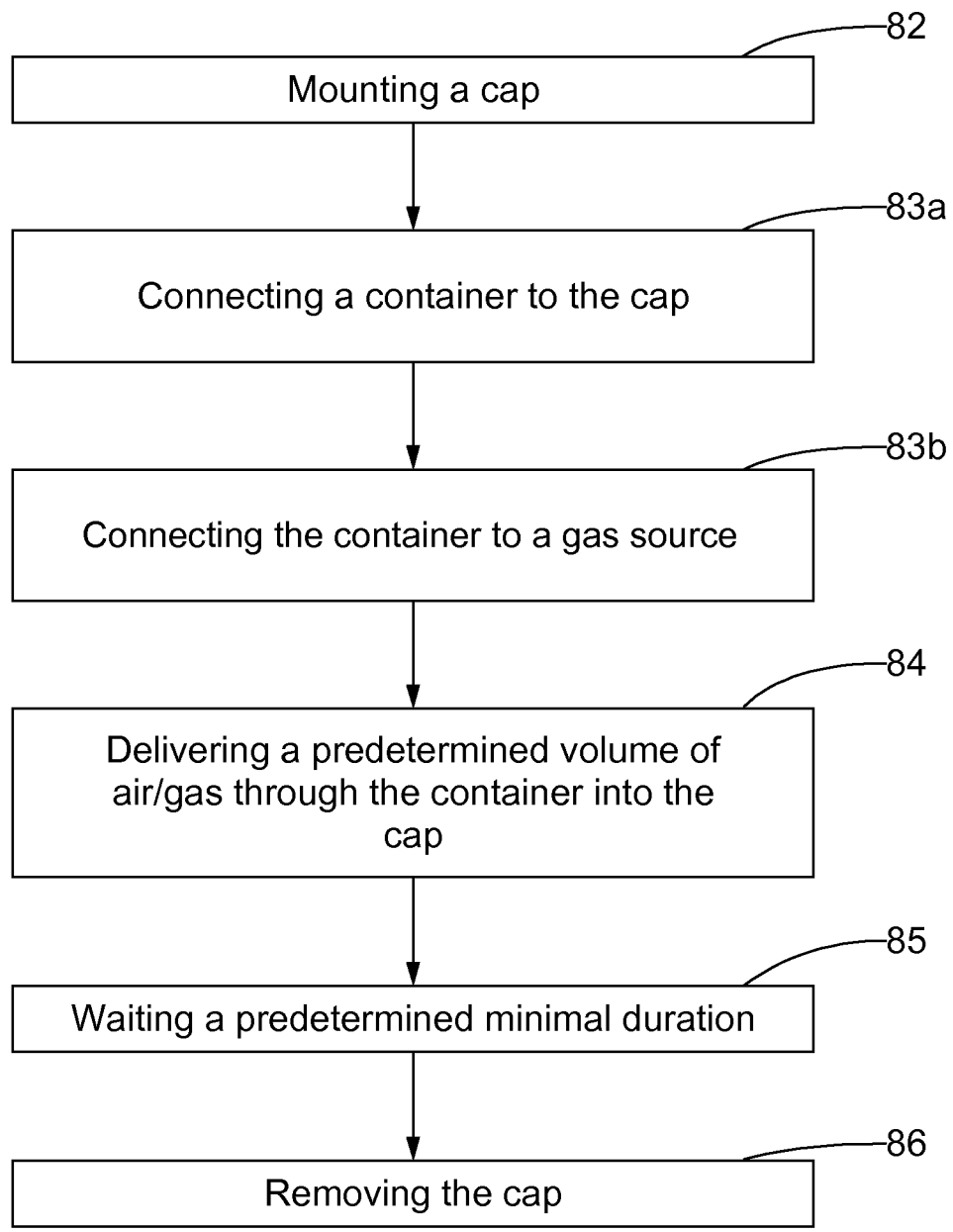
FIG. 6a is a flow charts that schematically illustrating of a method of treating lice and nits on a head of a patient, according to some embodiments of the present invention.

FIG. 6a is a flow chart that schematically illustrating of a method of treating lice and nits on a head 10 of a patient, according to some embodiments of the present invention, the method including the stages of:

(a) mounting a cap 17 over the head of the patient, the cap 17 includes an inlet tube 13, a distributor 17a, and injection tubes 17b, (stage 82);

(b) connecting a container 14' to the inlet tube 13, the container 14' includes an active agent 15 in liquid state absorbed in an immersed material 16, (stage 83a);

(c) connecting the container 14' to a vaporizing and circulating gas source 11, (stage 83b);

(d) delivering vaporizing and circulating gas 12 through the container 14', and evaporating the active agent 15, the vaporizing and circulating gas 12 may be air or another suitable gas, or a mixture of suitable gases, (stage 84);

(e) waiting at least a predetermined minimal duration, (stage 85); and (f) removing the cap 17 from the head 10 after the predetermined minimal duration, (stage 86).

Note: the order of performing some of the stages can differ from what is shown in the flow charts of the present illustration, particularly the order of stage 83a and stage 83b.

Figure 6B:
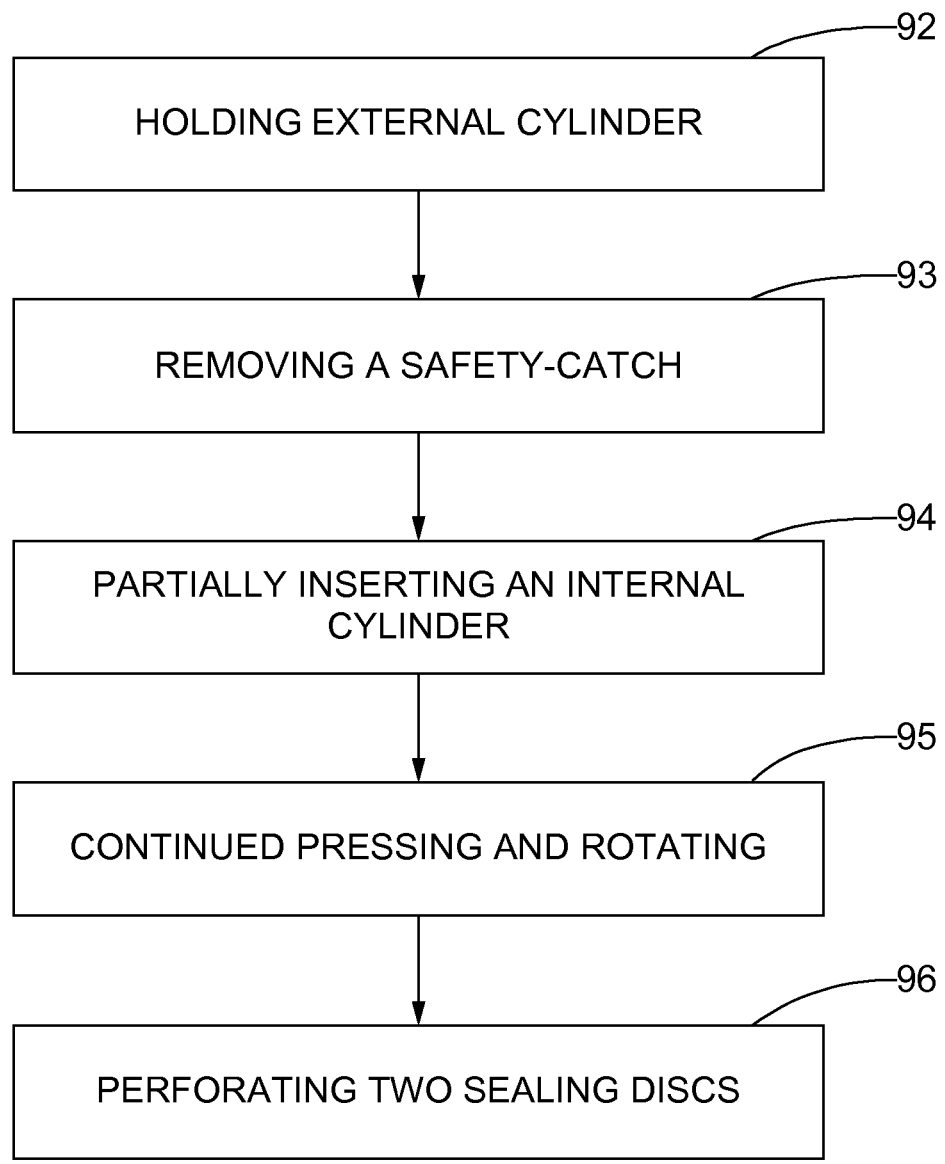
FIG. 6b is a flow charts that schematically illustrating of a method for connecting the container to the vaporizing and circulating gas source, according to a second embodiment of the present invention.

FIG. 6b is a flow charts that schematically illustrating a method for connecting the container 14' to the vaporizing and circulating gas source 11, which are sub-stages of stage 83b, according to a second embodiment of the present invention, the method including the sub-stages of:

(ci) holding external cylinder 20a of capsule 20, with the capsule 20 containing the container 14'', which contains active agent 15 and porous particles 16a, (sub-stage 92);

(cii) removing a safety-catch 21 from the capsule 20, (sub-stage 93);

(ciii) partially inserting an internal cylinder 20b, of the capsule 20 into an adapter 18, which includes an adapter tube 18c, (sub-stage 94);

(civ) after a performing a linear movement of the external cylinder (20a), the external cylinder second end (20aj) is halted within the adapter 18, and continuing pressing of external cylinder 20a in linear movement toward the adapter 18 and rotating it while adapter tracks 18f apply forces to the external cylinder outer clips 20ak until the linear and rotational movement between external cylinder 20a and adapter 18 are stopped and they are locked together by force of friction, as a result of the contact generated between external cylinder outer clip 20ak and adapter track stoppers 18g, (sub-stage 95); and (cv) in the course of the linear movement of the external cylinder 20a with regard to the internal cylinder 20b, perforating two sealing discs 14e'' to enable flow from and through container 14'' (sub-stage 96).

It has been found that for effective treatment, active agent 15 can be used at a time range of 5 seconds to 5 minutes, with the option for recurrent treatment in intervals of two to ten days. The quantity per treatment is of active agent 15, which in liquid state in storage takes up a volume of 0.5-5.0 cubic milliliters.

Figure 7:
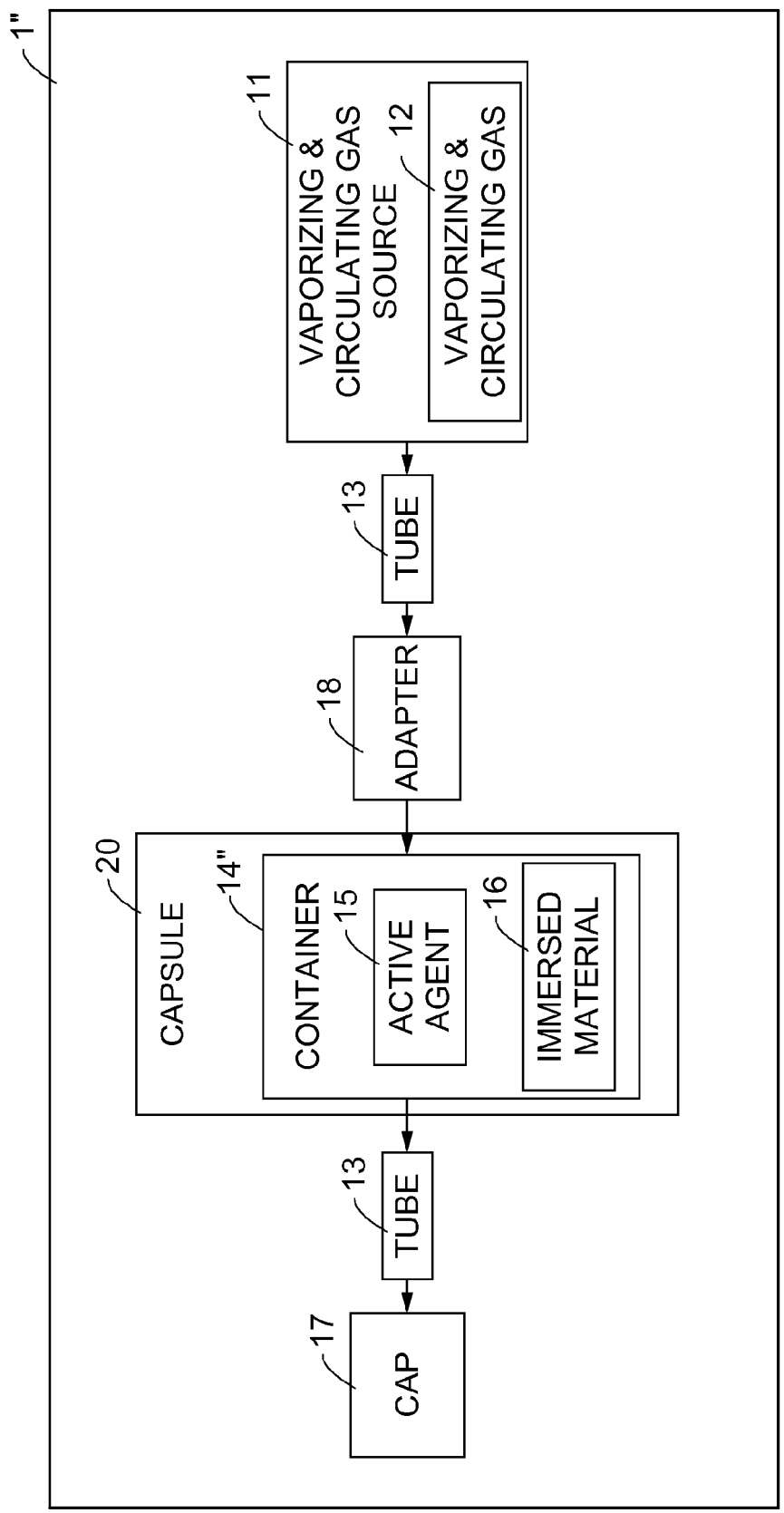
FIG. 7 is a schematic block diagram of a system for treating lice and nits, according to the second embodiment of the present invention.

FIG. 7 is a schematic block diagram of a system for treating lice and nits 1'', according to a second embodiment of the present invention.

The container 14'' is within a capsule 20. Prior to activation, for the purpose of performing treatment, capsule 20 is partially inserted into adapter 18, thus perforating seals and enabling flow of vaporizing and circulating gas 12 from a gas flow generator such as the vaporizing and circulating gas source 11 through the adapter 18 to the container 14''. Adapter 18 can be connected to circulating gas source 11 directly or by means of connecting tube 13.

The vaporizing and circulating gas 12 vaporizes active agent 15 and circulates it for the purpose of treating lice, through an additional connecting tube 13 to the cap 17.

Container 14'' can also contain an immersed material 16, such as porous particles.

FIG. 8 is an exploded isometric view schematic illustration of a capsule 20 and a safety-catch 21, according to the second embodiment of the present invention.

Capsule 20 includes the parts shown in the present illustration, the structure of each of which and its function, as well as the manner in which they compose capsule 20, and the manner in which they move and function will be described in further figures and their accompanying description.

The typical parts composing the capsule 20 are: an external cylinder 20*a*, an internal cylinder 20*b*, two sealing rings 20*c*, and a container 14". Container 14" includes a first carrier 14*j*, and a second carrier 14*k*, two sealing discs 14*e*", and two filters 14*l*'".

The safety-catch 21, when it is engaged with capsule 20, prevents movement between the external cylinder 20*a* and the internal cylinder 20*b* as will be further described in detail.

This list of parts is in no way limiting the present invention, and a capsule 20 including additional parts, less parts, and/or different parts is possible according to the present invention.

FIG. 9 is an isometric view schematic illustration of a connecting tube 13, according to the embodiments of the present invention.

Connecting tube 13 serves as a tube enabling flow of active agent 15 and of vaporizing and circulating gas 12 from the container 14" to the cap 17.

The connecting tube 13 can also serve as a tube enabling flow of vaporizing and circulating gas 12 from the vaporizing and circulating gas source 11 to container 14".

The option of using connecting tube 13 or connecting tubes 13 is in no way limiting the present invention, and connections can be made of the container 14" to the cap 17, and of the vaporizing and circulating gas source 11 to container 14", without mediation of connecting tubes 13.

(The vaporizing and circulating gas source 11, vaporizing and circulating gas 12, container 14", active agent 15, and cap 17, are not shown in the present illustration).

Its dimensions, such as internal and external diameter, and the material composing connecting tube 13 and its features such as rigidity, flexibility, plasticity, and impenetrability, resistibility to environmental conditions in storage and during suitable use are adapted for practical purposes.

FIG. 10 is an isometric view schematic illustration of an adapter 18 and an adapter seal 18*a*, according to the second embodiment of the present invention.

Adapter 18 enables connecting capsule 20, (not shown in the present drawing), to the vaporizing and circulating gas source 11, (not shown in the present drawing), directly, or by mediation of connecting tube 13, (not shown in the present drawing).

In addition, adapter 18 also assists in breaking seals of capsule 20, (not shown in the present drawing), in order to enable flow through it and from it, as will be further described.

Adapter seal 18*a* is designated to prevent leakage after the connection of capsule 20 to the adapter 18, in the area of the connection, however without disrupting flow between the parts.

Its external shape, from a top view of the adapter seal 18*a*, as well as its dimensions, conform to its designated location within adapter 18.

Figure 11A:
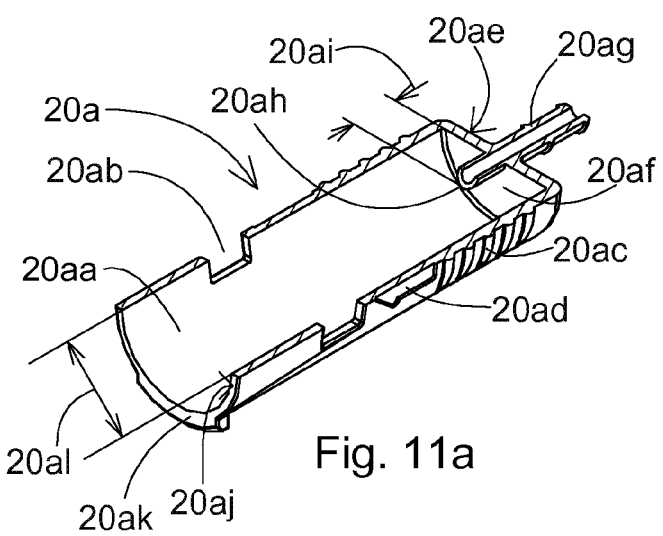
FIG. 11a is a cross sectional isometric view c-c illustration of an external cylinder of the second embodiment of the system for treating lice and nits, according to the present invention.

FIG. 11*a* is a cross sectional isometric view c-c illustration of an external cylinder 20*a* of the second embodiment of the system for treating lice and nits 1", according to the present invention.

Figure 14A:
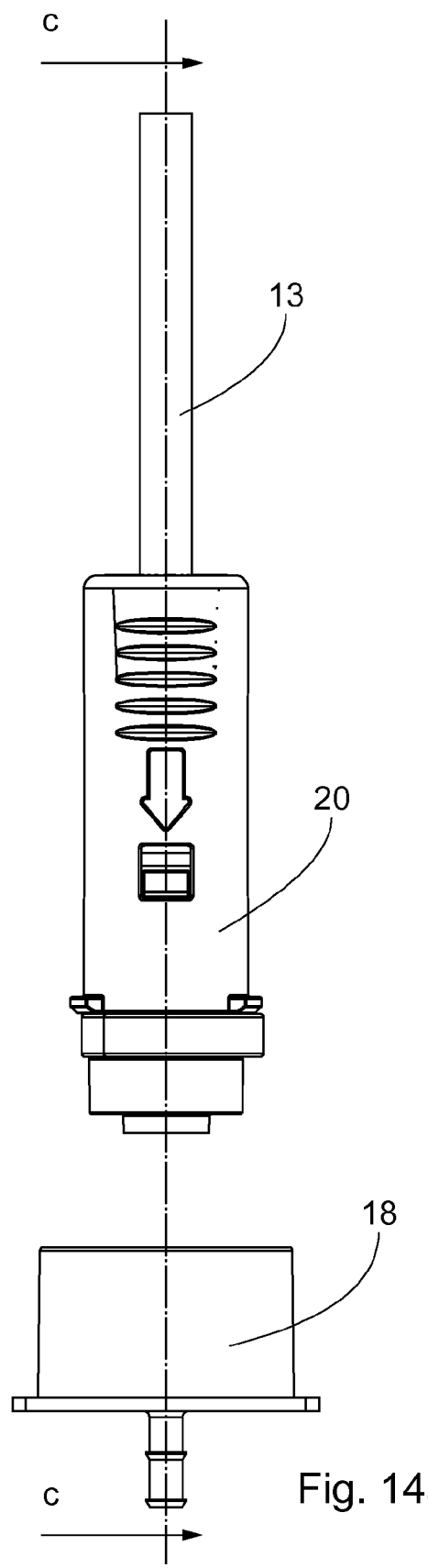
FIG. 14a is a side view schematic illustrations of a connecting tube, a capsule, and an adapter, of the second embodiment of the system for treating lice and nits, according to the present invention, upon which a section plane c-c is marked.

The cross section plane c-c can be found in FIG. 14*a*.

The external cylinder 20*a* also serves for holding by hand and transmitting forces during connection of capsule 20 to an adapter 18, (both not fully shown in the present drawing), and for the purpose of breaking both sealing discs 14*e*", (not shown in the present drawing).

The external cylinder 20*a* has an external cylinder wall 20*aa*, having two external cylinder windows 20*ab* designated to receive the internal cylinder hook heads 20*bba*, (not shown in the present drawings), during assembly of capsule 20, and to enable them a limited range of movement.

The external side of the external cylinder 20*a* has a gripping means 20*ac*, such as rigs or roughness, and an arrow mark 20*ad* indicating the direction of activating force when performing the connection to the adapter 18, (not shown in the present drawing).

The gripping means 20*ac* enables firm grip and marks the desired location for holding.

In the external cylinder first end 20*ae* there is an external cylinder end wall 20*af*, through which an external cylinder tube 20*ag* passes, and its end contained within the external cylinder 20*a* is an external cylinder piercer 20*ah*. The external cylinder tube 20*ag* has an external cylinder tube internal length 20*ai*.

The external cylinder tube 20*ag* enables connection of capsule 20 to a connecting tube 13, (both not fully shown in the present drawing).

In the external cylinder second end 20*aj* there are two external cylinder outer clips 20*ak*, (only one of which is shown in the present illustration), and which when connected in rotational movement of the capsule 20, (not shown in the present drawing), to the adapter 18, (not shown in the present drawing), is subject to force applied by adapter track 18*f*, (not shown in the present drawing), causing movement and perforation, as will be further described.

The external cylinder outer clips 20*ak*, and the adapter tracks 18*f* have a shape in a range of segments of spiral coils of identical pitch.

In other configurations according to the present invention, there can be a different number of external cylinder outer clips 20*ak*.

The external cylinder 20*a* has an external cylinder wall internal diameter 20*al*.

Figure 11D:
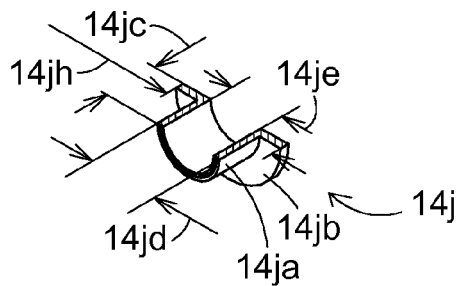
FIG. 11d is a cross sectional isometric view c-c illustration of a first carrier of the second embodiment of the system for treating lice and nits, according to the present invention.
Figure 11E:
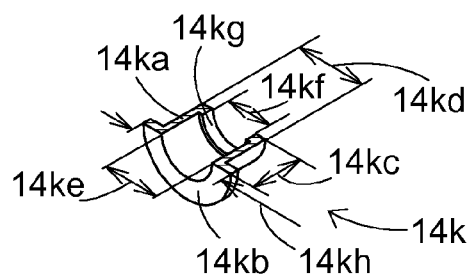
FIG. 11e is a cross sectional isometric view c-c illustration of a second carrier of the second embodiment of the system for treating lice and nits, according to the present invention.
Figure 11B:
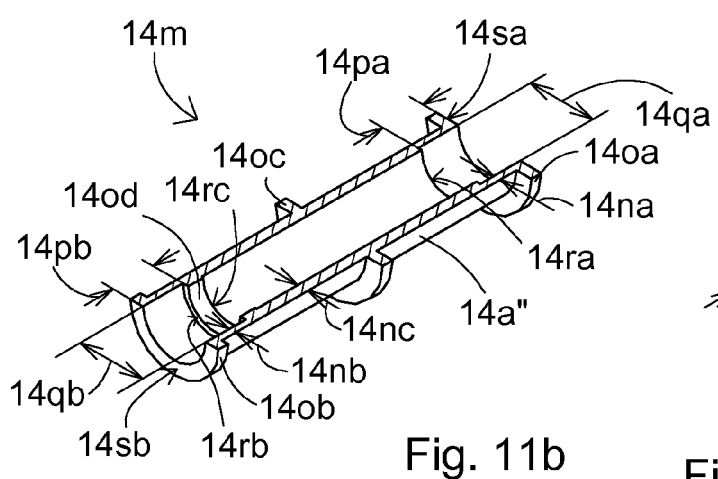
FIG. 11b is a cross sectional isometric view c-c illustration of a container cylinder of the second embodiment of the system for treating lice and nits, according to the present invention.

FIG. 11*b* is a cross sectional isometric view c-c illustration of a container cylinder 14*m* of the second embodiment of the system for treating lice and nits 1", according to the present invention.

The cross section plan c-c can be found in FIG. 14*a*.

The container cylinder 14*m* has a container main wall 14*a*" with a container first end 14*sa* and a container second end 14*sb*. The container main wall 14*a*" can have several wall thicknesses, such as a container main wall first thickness 14*na*, in a segment starting with container first end 14*sa* and continuing to a depth of a container first stair depth 14*pa*, a container main wall second thickness 14*nb*, in a segment starting with container second end 14*sb* and continuing to a depth of a container second stair depth 14*pb*, a location in which a container interior ring 14*od* is disposed, and a container main wall third thickness 14*nc*, which is thicker than both of the aforementioned thicknesses, and is along the remainder of the container main wall.

The container interior ring 14*od* serves as a stair that provides a rest for the first carrier 14*j* (not shown in the present drawing) and enables convenient sealing with the sealing ring 20*c* (not shown in the present drawing) and adhesion of the sealing disc 14*e*" (not shown in the present drawing).

The container first internal stair 14*ra* serves as a support for one filter 14*l*'", and the container second internal stair 14*rb* serves as a support for another filter 14*l*'", (both filters 14*l*'" not shown in the present drawing).

As a result, the container cylinder 14*m*, in the configuration shown in the present illustration, includes three internal stairs, a container first internal stair 14*ra*, a container second internal stair 14*rb*, and a container third internal stair 14*rc*.

Likewise, the container main wall 14*a*" bears outer rings, three in the configuration shown in the present illustration, a container first outer ring 14*oa* at the container first end 14*sa*, a container second outer ring 14*ob* at the container second end 14*sb*, and a container third outer ring 14*oc* in between.

Figure 14B:
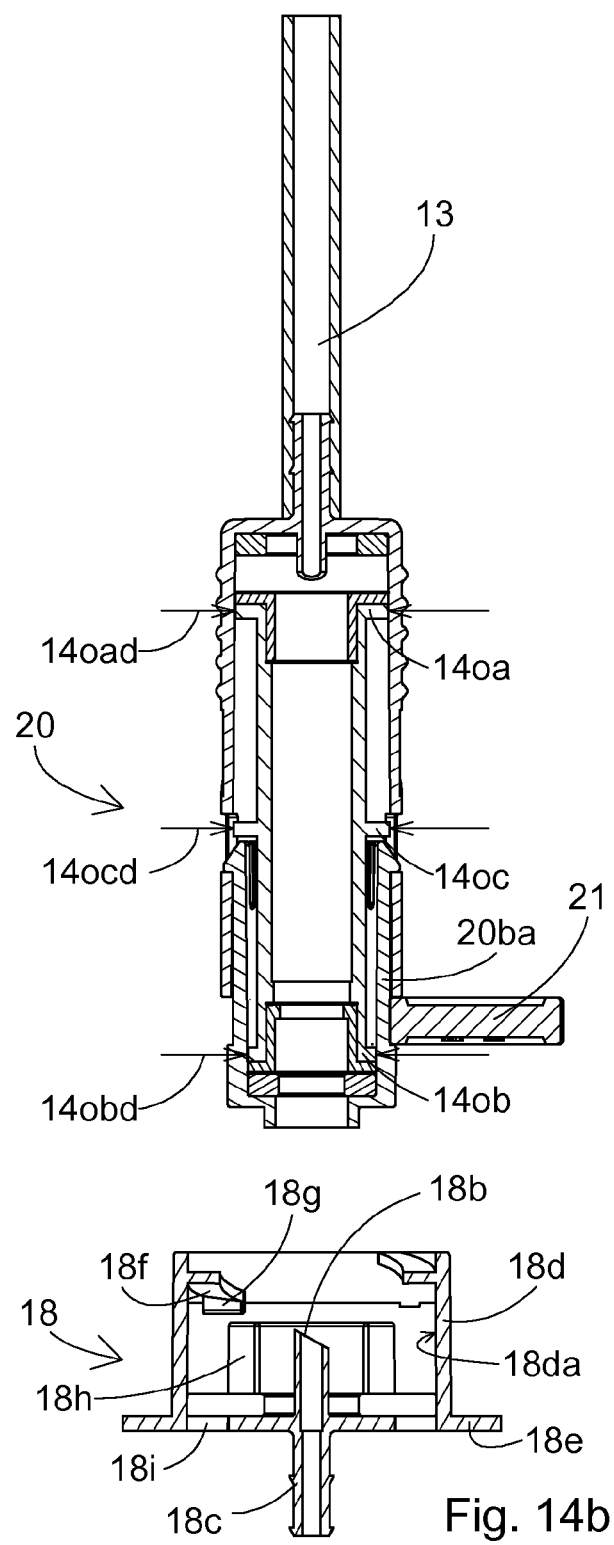
FIG. 14b is a cross sectional view c-c illustration of a connecting tube, a capsule, a safety-catch, and an adapter, of the second embodiment of the system for treating lice and nits, according to the present invention.

Each one of the container outer rings 14*oa*, 14*ob*, and 14*oc* has a container outer ring diameter marked in FIG. 14*b*, conforming to the dimensions of other elements composing capsule 20.

In the segment between the container first end 14*sa* and the container first internal stair 14*ra*, the length of which is the container first stair depth 14*pa*, container main wall 14*a*" has a container first internal diameter 14*qa*.

In the segment between the containers second end 14*sb* and the container second internal stair 14*rb*, the length of which is the container second stair depth 14*pb*, container main wall 14*a*" has a container second internal diameter 14*qb*.

The container first outer ring 14*oa* serves as a support for first carrier 14*j* and for good grip of one filter 14*l*" between them, (both not shown in the present drawing).

Similarly, the container second outer ring 14*ob* serves as a support for the second carrier 14*k* and the filter 14*l*" between them, (both not shown in the present drawing).

The container third outer ring 14*oc* helps to fix the container cylinder 14*m* inside the external cylinder 20*a*, (not shown in the present drawing), and furthermore enables the internal cylinder 20*b*, (not shown in the present drawing), to push the container cylinder 14*m* in order to cause the puncturing of a seal, as will be further detailed.

Figure 11C:
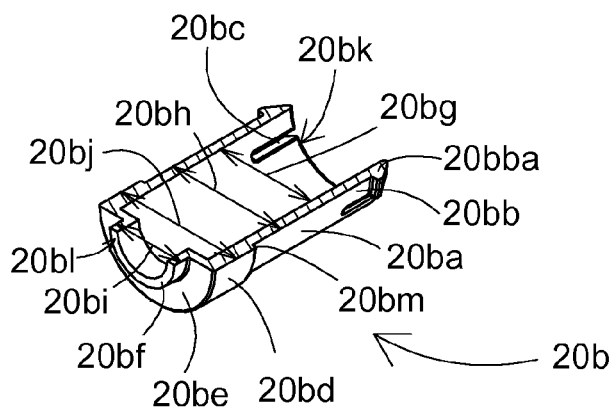
FIG. 11c is a cross sectional isometric view c-c illustration of an internal cylinder, of the second embodiment of the system for treating lice and nits, according to the present invention.

FIG. 11*c* is a cross sectional isometric view c-c illustration of an internal cylinder 20*b*, of the second embodiment of the system for treating lice and nits 1", according to the present invention.

The cross section plane c-c can be found in FIG. 14*a*.

The internal cylinder 20*b*, has an internal cylinder wall 20*ba* having two ends, an internal cylinder first end 20*bk* and an internal cylinder second end 20*bl*.

From the internal cylinder first end 20*bk* exits along the internal cylinder wall 20*ba* four internal cylinder slots 20*bc*, two of which are shown in the present illustration, emerge from the internal cylinder first end 20*bk* along the internal cylinder wall 20*ba*.

In other configurations, there can be more or less internal cylinder slots 20*bc*.

Between two adjacent internal cylinder slots 20*bc*, there is an elastic internal cylinder hook 20*bb*. This elasticity enables, during the assembly of capsule 20, (not shown in the present drawing), to dispose each internal cylinder hook head 20*bba* within an external cylinder window 20*ab*, (not shown in the present drawing), thus limiting the range of movement between the internal cylinder 20*b* and the external cylinder 20*a*, (not shown in the present drawing).

On the internal cylinder wall 20*ba*, at its more distant end from the internal cylinder first end 20*bk*, there is an internal cylinder outer ring 20*bd*, which is attached to an internal cylinder base 20*be*, which is attached to an internal cylinder base ring 20*bf*.

The internal cylinder base 20*be* presses on the adapter seal 18*a*, (not shown in the present drawing), after the connection of capsule 20 to the adapter 18, (both not shown in the present drawing), thus achieving a good seal between them.

Near the closer end of the internal cylinder 20*b* to the internal cylinder base 20*be* there is an internal cylinder outer stair 20*bm*, which prevents movement of container 14" into the external cylinder 20*a*, when a safety-catch 21, (both not shown in the present drawing) is assembled to the container cylinder 14*m*, thus preventing the puncturing of seals.

Note: use of terms such as: located, attached, disposed, etc., are not in any way limiting to a specific combination of components, and according to the present invention there can be a system including various elements made of a single continuous material, which can be manufactured in a process suitable for designing its shape and attaining additional features, such as casting or machining.

For the dimensions of internal cylinder 20*b* to conform to other elements composing capsule 20, the following specific dimensions are particularly significant, and are indicated in the present illustration: the internal cylinder wall internal diameter 20*bg*, the internal cylinder wall exterior diameter 20*bh*, the internal cylinder base ring exterior diameter 20*bi*, and the internal cylinder outer ring outer diameter 20*bj*.

When in the description and in the claims sections of the present patent application reference is made to the diameters of two components mounted one within the other, using the term substantially, or the like, such as in the following phrasing: "a first element having a diameter substantially equal to the diameter of a second element", the reference is to dimensions which are very close in size, however maintain a small gap between both diameters, several orders of magnitude smaller than the dimensions of the diameters. The dimensions of the diameters and the possible tolerance are in these cases as is acceptable in engineering design to ensure that there will be longitudinal movement between both of the components in question, without excessive friction, however at the same time without excessive lateral freedom of movement.

This reference also applies to length dimensions and angular dimensions of segments of components.

FIG. 11*d* is a cross sectional isometric view c-c illustration of a first carrier 14*j* of the second embodiment of the system for treating lice and nits 1", according to the present invention.

The cross section plane c-c can be found in FIG. 14*a*.

First carrier 14*j* has a spatial form including a first carrier cylinder 14*ja*, one of whose ends has a first carrier disc 14*jb*. The first carrier cylinder 14*ja* and the first carrier disc 14*jb* have a first carrier interior diameter 14*je*, and the first carrier cylinder 14*ja* has a first carrier cylinder exterior diameter 14*jd*. The first carrier 14*j* has a first carrier length 14*jc*.

The first carrier 14*j* serves as a support for filter 14*l*" and to a sealing disc 14*e*", (both not shown in the present drawing), disposed at two opposite ends of it.

The dimension of the first carrier length 14*jc* is sufficiently long in order to prevent puncturing of sealing disc 14*e*" by the external cylinder piercer 20*ah*, (not shown in the present drawing), even when there is relative movement between them.

The dimensions of the first carrier cylinder exterior diameter 14*jd* and the container first internal diameter 14*qa* are substantially equal.

The first carrier 14*j* has a first carrier ring disc exterior diameter 14*jh*.

FIG. 11*e* is a cross sectional isometric view c-c illustration of a second carrier 14*k* of the second embodiment of the system for treating lice and nits 1", according to the present invention.

The cross section plane c-c can be found in FIG. 14*a*.

Second carrier 14*k* has a spatial form including a second carrier cylinder 14*ka* one of whose ends has a second carrier disc 14*kb*, while the opposite end has a second carrier ring 14*kg* having second carrier ring diameter 14*kf*.

According to another variation the second carrier 14*k* does not include a second carrier ring 14*kg* and it is identical in shape to the first carrier 14*j* (not shown in the present drawing), with the single difference being in the dimensions of the second carrier ring disc exterior diameter 14*kh*, which conform to internal cylinder wall internal diameter 20*bg*, and the first carrier ring disc exterior diameter 14*jh*, which conforms to the external cylinder wall internal diameter 20*al*.

The second carrier cylinder 14*ka* and the second carrier disc 14*kb* have a second carrier interior diameter 14*ke*, and the second carrier cylinder 14*ka* has a second carrier cylinder exterior diameter 14*kd*. The second carrier 14*k* has a second carrier length 14*kc*.

The second carrier 14*k* serves as a support for a 14*l*" and a sealing disc 14*e*", (both not shown in the present drawing), both disposed at its opposite ends.

The dimension of the second carrier length 14*kc* is long enough to prevent puncturing of sealing disc 14*e*" by the adapter piercer 18*b*, (both not shown in the present drawing), even when there is relative movement between them.

The dimensions of the second carrier cylinder exterior diameter 14*kd* and the container second internal diameter 14*qb* are substantially equal.

Figure 12:
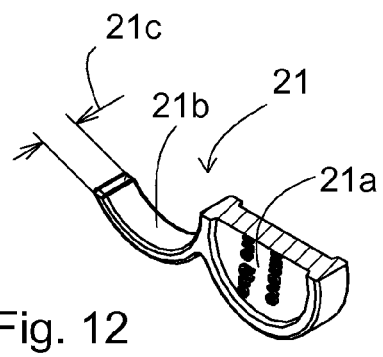
FIG. 12 is a cross sectional isometric view c-c illustration of a safety-catch of the second embodiment of the system for treating lice and nits, according to the present invention.

FIG. 12 is a cross sectional isometric view c-c illustration of a safety-catch 21 of the second embodiment of the system for treating lice and nits 1", according to the present invention.

The cross section plane c-c can be found in FIG. 14*a*.

The safety-catch 21 includes a safety-catch handle 21*a* and two safety-catch stopper arms 21*b*, one of which is shown in the present illustration.

The safety-catch stopper arms 21*b* is retractable, thus enabling manual removal of the safety-catch 21 by pulling the safety-catch handle 21*a*. The safety-catch stopper arms 21*b* have a safety-catch stopper arm width 21*c*, which conforms to the distance of movement the safety-catch 21 covers between the external cylinder 20*a* and the internal cylinder 20*b*, (both not shown in the present drawing).

Figure 13:
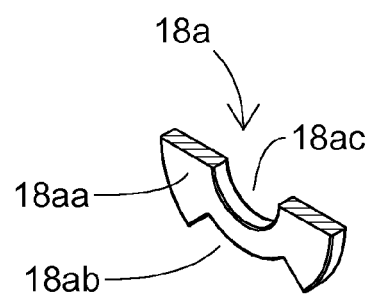
FIG. 13 is a cross sectional isometric view c-c illustration of an adapter seal of the second embodiment of the system for treating lice and nits, according to the present invention.

FIG. 13 is a cross sectional isometric view c-c illustration of an adapter seal 18*a* of the second embodiment of the system for treating lice and nits 1", according to the present invention.

The cross section plane c-c can be found in FIG. 14*a*.

The adapter seal 18*a* has an adapter seal body 18*aa*, the perimeter of which has two adapter seal niches 18*ab*, one of which is shown in the present illustration, whose shape, from a top view, is conform with the shape of the adapter inner cylinder segment 18*h*, (not shown in the present drawing), also from a top view, and at its center, from a top view, is an adapter seal hole 18*ac*.

FIG. 14*a* is a side view schematic illustrations of a connecting tube 13, a capsule 20, and an adapter 18, of the second embodiment of the system for treating lice and nits 1", according to the present invention, upon which a section plane c-c is marked.

The connecting tube 13 shown in the present illustration is designated to connect the capsule 20 to a cap 17, (not shown in the present drawing), and can be made of a flexible material.

The state shown in the present illustration is inactive, in which the capsule 20 and the adapter 18 are separated from each other.

FIG. 14*b* is a cross sectional view c-c illustration of a connecting tube 13, a capsule 20, a safety-catch 21 and an adapter 18, of the second embodiment of the system for treating lice and nits 1", according to the present invention.

The container first outer ring 14*oa* has a container first outer ring diameter 14*oad*, the container second outer ring 14*ob* has a container second outer ring diameter 14*obd*, and the container third outer ring 14*oc* has a container third outer ring diameter 14*ocd*. The container first outer ring diameter 14*oad*, the container second outer ring diameter 14*obd* are substantially equal in size to the external cylinder wall internal diameter 20*al*, (not shown in the present drawing), and the container third outer ring diameter 14*ocd* is substantially equal in size to the internal cylinder wall internal diameter 20*bg*.

The safety-catch 21 is shown mounted on the internal cylinder wall 20*ba*.

The adapter 18 has adapter base 18*e*, this base can be a wall of the vaporizing and circulating gas source 11, (not shown in the present drawing), or a separate wall, with the adapter 18 and the vaporizing and circulating gas source 11 being connected to each other by means of a connecting tube 13, in this case the shape from a top view of the adapter base 18*e* can be circular.

The adapter base 18*e* is connected to an adapter outer cylinder 18*d* and an adapter inner cylinder segment 18*h*, and between them, on part of the adapter base 18*e*, there are adapter base opening segments 18*i*.

The adapter base opening segments 18*i* are designated to facilitate the manufacturing of the adapter tracks 18*f* with the adapter track stoppers 18*g*. This applies to various methods of manufacturing, including casting and machining.

An adapter tube 18*c* passes through adapter base 18*e* and its end which is internal relative to adapter 18 is pointed and serves as an adapter piercer 18*b*.

When the adapter 18 and the vaporizing and circulating gas source 11 are connected to each other directly and without mediation of a connecting tube 13, there is no need for the part of the adapter tube 18*c*, which protrudes beneath the adapter base 18*e* in the orientation shown in the present illustration.

The adapter outer cylinder inner face 18*da* is connected to two adapter tracks 18*f*, at the end of each of which is an adapter track stopper 18*g*.

FIG. 15*a* is a side view schematic illustrations of a capsule 20, and an adapter 18, of the second embodiment of the system for treating lice and nits 1", engaged with each other, according to the present invention, upon which a section plane d-d is marked.

FIG. 15*b* is a cross sectional view d-d illustration of a capsule 20, and an adapter 18, of the second embodiment of the system for treating lice and nits 1", engaged with each other, according to the present invention.

During movement of the external cylinder 20*a* in the direction −Z relative to the adapter 18, the external cylinder piercer 20*ah* pierces a puncture in one sealing disc 14*e*", and the adapter piercer 18*b* pierces a puncture in the second sealing disc 14*e*'".

Figure 17A:
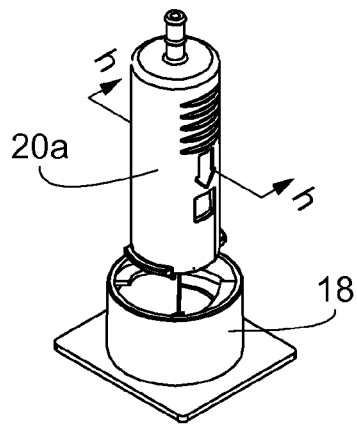
FIG. 17a is an isometric view schematic illustration of an external cylinder and of an adapter of the second embodiment of the system for treating lice and nits, according to the present invention, upon which a section plane h-h is marked.
Figure 17C:
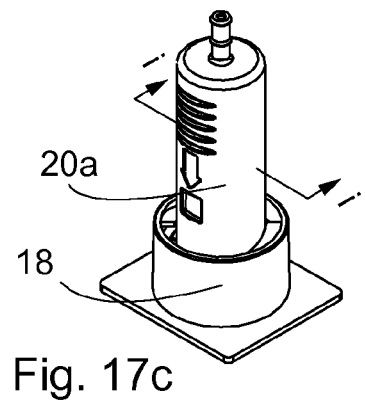
FIG. 17c is an isometric view schematic illustration of an external cylinder and of an adapter of the second embodiment of the system for treating lice and nits, according to the present invention, upon which a section plane i-i is marked.
Figure 17B:
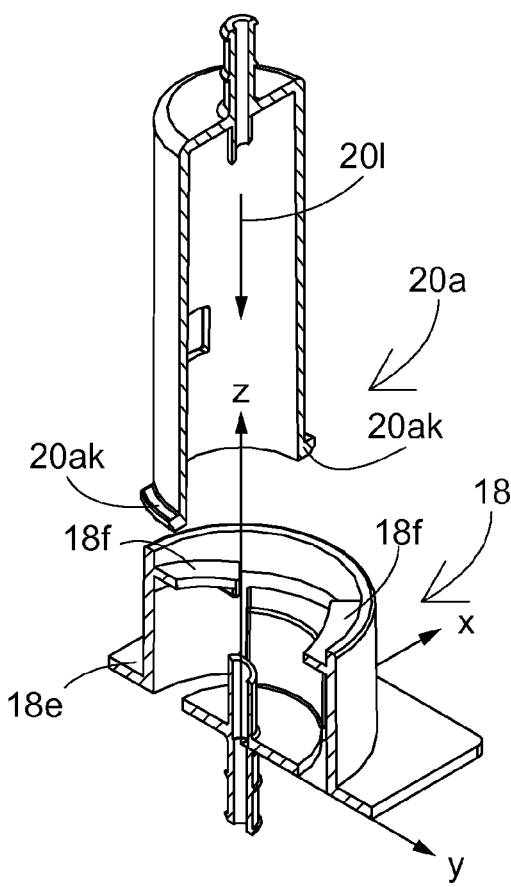
FIG. 17b is a cross sectional view h-h illustration of the external cylinder and of the adapter of the second embodiment of the system for treating lice and nits, according to the present invention.

Axis Z is one axis of a Cartesian X, Y, and Z axis system defined in FIG. 17*b*.

These punctures enable flow. However, the external cylinder piercer 20*ah* and the adapter piercer 18*b* do not pierce both filters 14*l*", thanks to a combination of length dimensions, also including the dimensions of the first carrier length 14*jc* and the second carrier length 14*kc*.

The present illustration also shows the adapter seal 18*a*.

FIG. 15*c* is a front view schematic illustration of a capsule 20, and an adapter 18, of the second embodiment of the system for treating lice and nits 1", engaged with each other, according to the present invention, upon which a section plane e-e is marked.

FIG. 15*d* is a cross sectional view e-e illustration of a capsule 20, and an adapter 18, of the second embodiment of the system for treating lice and nits 1", engaged with each other, according to the present invention.

The movement of the external cylinder 20*a* in the direction −Z relative to the adapter 18 is achieved thanks to manual pushing of the external cylinder 20*a* into the adapter 18, followed by its rotation toward an external cylinder rotational direction 20r of the external cylinder 20a relative to the adapter 18 around coordinate Z.

Each external cylinder outer clip 20ak is forced by an adapter track 18f to keep applying force in the direction –Z, and thanks to the forces applied between the various elements, create a lock of the external cylinder 20a within the adapter 18.

The present illustration also shows the adapter seal 18a.

Figure 16A:
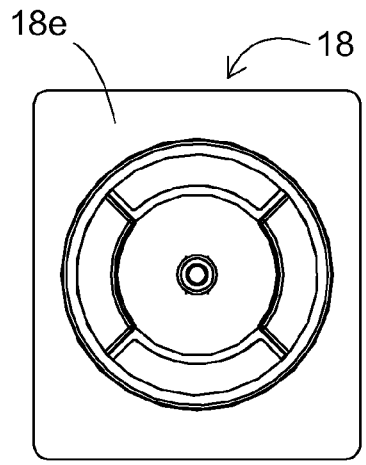
FIG. 16a is a top view schematic illustration of an adapter, of the second embodiment of the system for treating lice and nits, according to the present invention.

FIG. 16a is a top view schematic illustration of an adapter 18, of the second embodiment of the system for treating lice and nits 1", according to the present invention.

The adapter base 18e has a rectangular shape, however the present invention is in no way limited strictly to this shape, and other shapes are also possible.

Figure 16D:
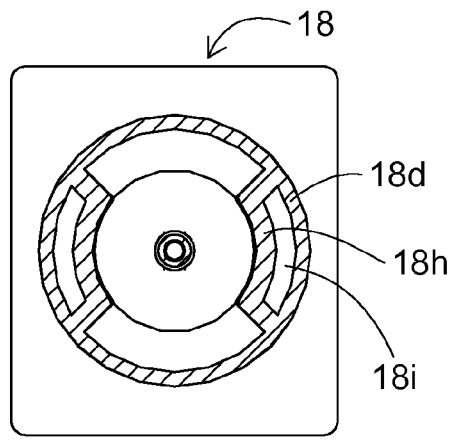
FIG. 16d is a cross sectional view f-f illustration of the second embodiment of the system for treating lice and nits, according to the present invention.
Figure 16B:
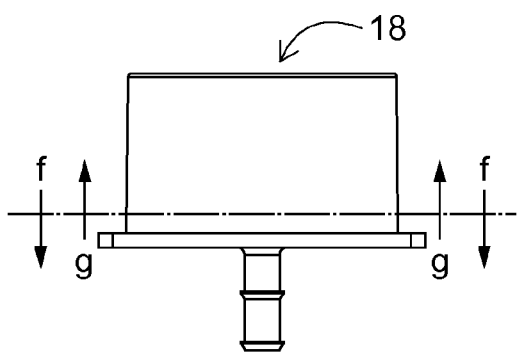
FIG. 16b is a front view schematic illustration of an adapter of the second embodiment of the system for treating lice and nits, according to the present invention, upon which a section planes g-g and f-f are marked.

FIG. 16b is a front view schematic illustration of an adapter 18 of the second embodiment of the system for treating lice and nits 1", according to the present invention, upon which a section planes g-g and f-f are marked.

Figure 16E:
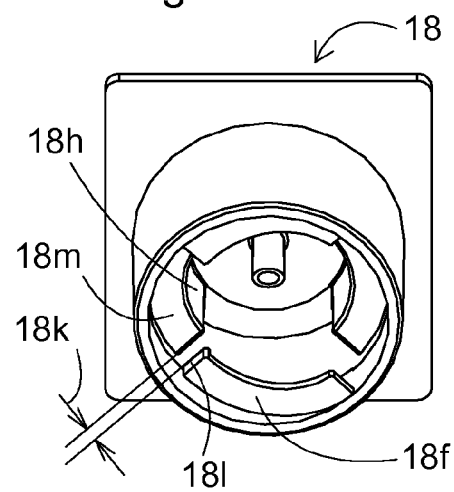
FIG. 16e is a top isometric view schematic illustration of an adapter, of the second embodiment of the system for treating lice and nits, according to the present invention.
Figure 16C:
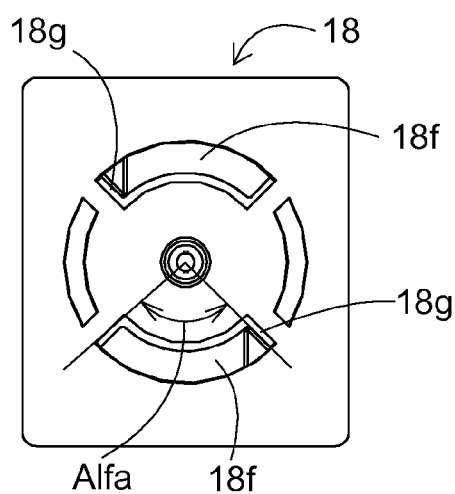
FIG. 16c is a bottom view schematic illustration of an adapter, of the second embodiment of the system for treating lice and nits, according to the present invention.

FIG. 16c is a bottom view schematic illustration of an adapter 18, of the second embodiment of the system for treating lice and nits 1", according to the present invention.

At the end of each one of the adapter tracks 18f there is an adapter track stopper 18g. Each adapter track 18f has the shape of a segment of a spiral coil, which from a top view has an adapter track segment angle Alfa, a good value of which is of the order of magnitude of 90 degrees.

FIG. 16d is a cross sectional view f-f illustration of the second embodiment of the system for treating lice and nits 1", according to the present invention.

Between the adapter outer cylinder 18d and the adapter inner cylinder segment 18h, there is an adapter base opening segment 18i.

FIG. 16e is a top isometric view schematic illustration of an adapter 18, of the second embodiment of the system for treating lice and nits 1", according to the present invention.

Above each adapter inner cylinder segment 18h there is an adapter inner stair 18m. The present illustration shows the spiral nature of adapter track 18f. Between adapter track free end 18l and adapter inner stair 18m, there is an adapter track inner cylinder segment gap 18k, which is suitable for passing through in rotational movement of an external cylinder outer clip 20ak, (not shown in the present drawing).

Figure 16F:
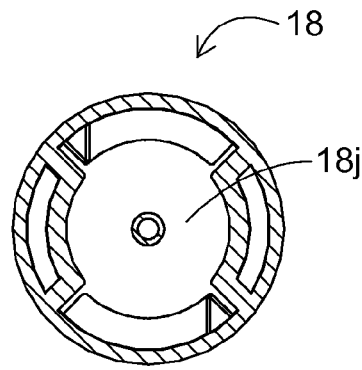
FIG. 16f is a cross sectional view g-g illustration of the second embodiment of the system for treating lice and nits.

FIG. 16f is a cross sectional view g-g illustration of the second embodiment of the system for treating lice and nits 1".

An adapter inner space 18j enables inserting an end of a capsule 20, (not shown in the present drawing), into the adapter 18, for the purpose of their connection.

FIG. 17a is an isometric view schematic illustration of an external cylinder 20a and of an adapter 18 of the second embodiment of the system for treating lice and nits 1", according to the present invention, upon which a section plane h-h is marked.

The external cylinder 20a and the adapter 18 are not engaged with each other, and are shown here in a smaller size than shown in the majority of illustrations of the present patent application, for purposes of convenience.

FIG. 17b is a cross sectional view h-h illustration of the external cylinder 20a and of the adapter 18 of the second embodiment of the system for treating lice and nits 1", according to the present invention.

For the purpose of better understanding the relative movements between the external cylinder 20a and the adapter 18 when they are engaged with each other, a Cartesian X, Y, and Z axis system is defined, attached to the adapter 18. Its Z axis serves as the adapter's symmetry axis, and plane X-Y is placed on the bottom side of the adapter base 18e.

The external cylinder 20a is shown in the present illustration rotated at 90 degrees around axis Z relative to the original section plane.

Prior to the engagement of the external cylinder 20a with the adapter 18, the external cylinder 20a is above the adapter 18, according to the defined axis system, in such an orientation that external cylinder outer clip 20ak is not above an adapter track 18f. The engagement process starts with moving the capsule 20, which for the purpose of simplicity is presented here by only the external cylinder 20a, in movement shown here as external cylinder linear movement 20l in a direction along axis Z, and in a direction opposite to its direction.

FIG. 17c is an isometric view schematic illustration of an external cylinder 20a and of an adapter 18 of the second embodiment of the system for treating lice and nits 1", according to the present invention, upon which a section plane i-i is marked.

The external cylinder 20a and the adapter 18 are engaged with each other and shown here as smaller than they are shown in the majority of illustrations of the present illustration, for purposes of convenience.

Figure 17D:
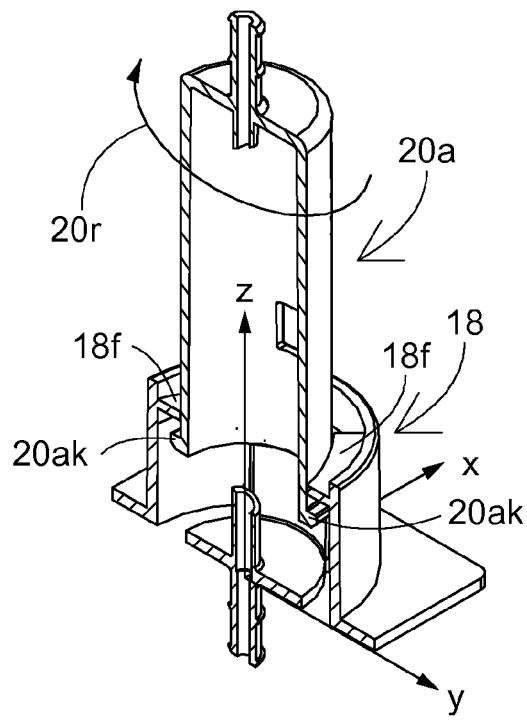
FIG. 17d is a cross sectional view i-i illustration of the external cylinder and of the adapter of the second embodiment of the system for treating lice and nits according to the present invention.

FIG. 17d is a cross sectional view i-i illustration of the external cylinder 20a and of the adapter 18 of the second embodiment of the system for treating lice and nits 1", according to the present invention.

After the external cylinder 20a has been inserted sufficiently deep into the adapter 18 it is manually rotated in the direction marked by the external cylinder rotational direction 20r. In this state, the adapter tracks 18f force the external cylinder outer clip 20ak to maintain the linear movement of the external cylinder 20a until it is locked.

Figure 18A:
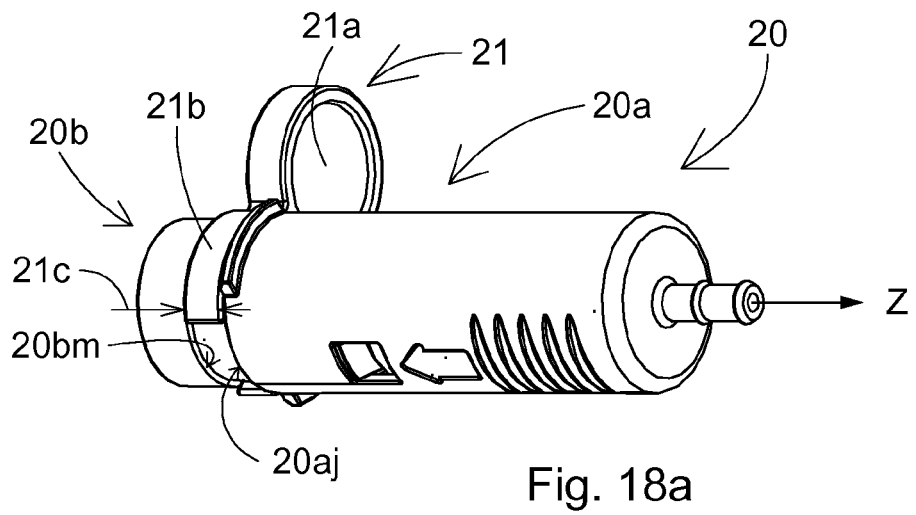
FIG. 18a is an isometric view schematic illustration of a capsule onto which is mounted a safety-catch, of the second embodiment of the system for treating lice and nits, according to the present invention.

FIG. 18a is an isometric view schematic illustration of a capsule 20, onto which is mounted a safety-catch 21, of the second embodiment of the system for treating lice and nits 1", according to the present invention.

The safety-catch 21 is shown in the present illustration as engaged with capsule 20. The two safety-catch stopper arms 21b are in the gap between the internal cylinder outer stair 20bm and the external cylinder second end 20aj whose size substantially equals the safety-catch stopper arm width 21c, thus preventing relative closing movement along axis Z between the external cylinder 20a and the internal cylinder 20b.

Figures 18B, 18C:
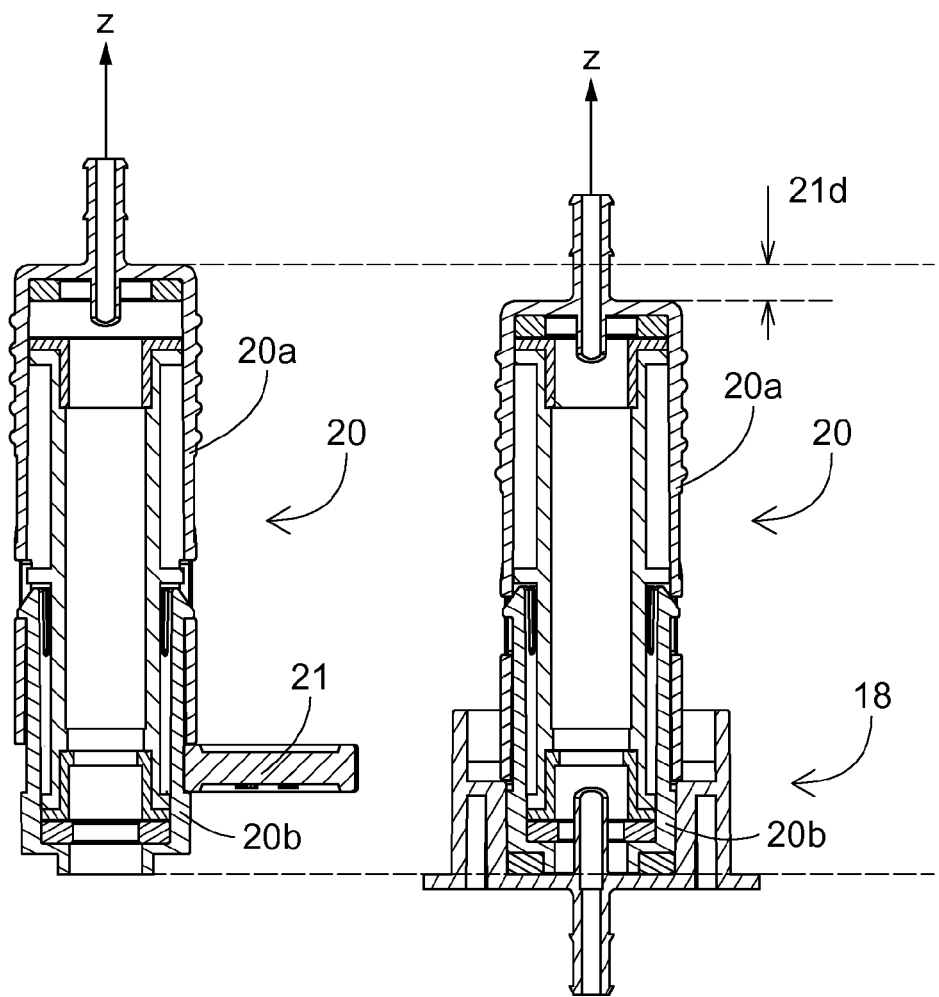
FIG. 18b is a cross sectional view c-c illustration of a capsule, and a safety-catch of the second embodiment of the system for treating lice and nits, according to the present invention.
FIG. 18c is a cross sectional view d-d illustration of a capsule, and an adapter, of the second embodiment of the system for treating lice and nits, engaged with each other, according to the present invention.

FIG. 18b is a cross sectional view c-c illustration of a capsule 20, and a safety-catch 21, of the second embodiment of the system for treating lice and nits 1", according to the present invention.

The safety-catch 21 prevents relative closing movement along axis Z between the external cylinder 20a and the internal cylinder 20b.

FIG. 18c is a cross sectional view d-d illustration of a capsule 20 and an adapter 18, of the second embodiment of the system for treating lice and nits 1", engaged with each other, according to the present invention.

After withdrawal of the safety-catch 21, (not shown in the present drawing), from capsule 20 and pressing capsule 20 toward the adapter 18 in the direction –Z, closing movement is achieved in this direction of the external cylinder 20a relative to the internal cylinder 20b. This movement cannot be larger than the value of an external cylinder movement range 21d.

Figure 19:
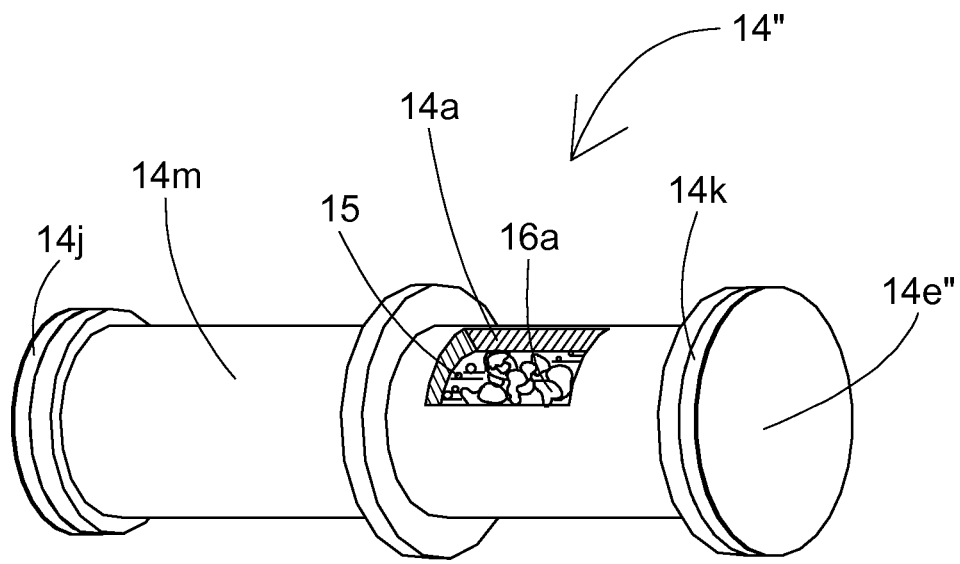
FIG. 19 is an isometric view schematic illustration of a container, of the second embodiment of the system for treating lice and nits, according to the present invention.

FIG. 19 is an isometric view schematic illustration of a container 14", of the second embodiment of the system for treating lice and nits 1", according to the present invention.

The container 14" includes container cylinder 14m, a first carrier 14j, a second carrier 14k, and two sealing discs 14e", and for as long as a sealing disc 14e" has not been punctured, the container 14" contains active agent 15.

Furthermore, according to an embodiment of the present invention, it contains immersed material 16, which in the present illustration includes a plurality of porous particles 16a. Strictly for the purpose of showing the active agent 15 and the porous particles 16a in the present illustration, part of the container main wall 14a" has been removed.

The plurality of porous particles 16a enables preserving the active agent 15 in liquid state during storage, and enables fast vaporization of the active agent 15 when vaporizing and circulating gas 12, (not shown in the present illustration), flows through the container 14".

The vaporization rate is dependent on several parameters also including: surface areas, the type of liquid, (the active agent 15), the flow speed of the vaporizing and circulating gas 12 and the temperature of the active agent 15.

According to the present invention, different kinds of vaporizing and circulating gas 12 can be used, also including Butane, Freon, and Nitrous Oxide.

Adding organic and non-organic solvents materials, such as acetone or ethanol, to vaporizing and circulating gas 12 has been found to expedite the vaporizing rate of the active agent 15.

Figure 20:
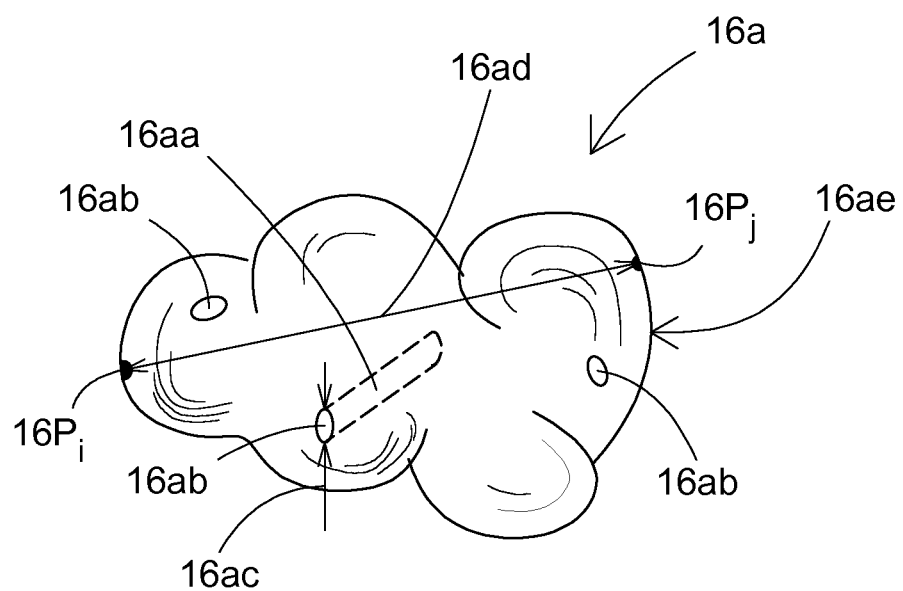
FIG. 20 is an isometric view schematic illustration of a porous particle.

FIG. 20 is an isometric view schematic illustration of a porous particle 16a.

The porous particle 16a is an inert component, miniscule relative to the dimensions of the container 14, having pores 16aa. Each pore 16aa has at least one pore opening 16ab, having an opening diameter 16ac in the order of magnitude of single to several tens of microns. The porous particle 16a has a porous particle size 16ad in the order of magnitude of several tens to several hundreds of microns. The porous particle size 16ad is the largest distance between two surface points 16p upon porous particle surface 16ae. The porous particle 16a can be amorphous or of a defined spatial shape, such as a cylinder, a sphere, etc., and it can be composed of materials such as thermoplastic polymers, glass, etc.

To remove any doubt, note that the manner in which the elements of the present invention are described in the illustrations can be highly detailed, however is not in any way limiting the present illustration, however is for the purpose of clarification and furthering understanding. The present invention can be implemented in embodiments that differ from the specification given with regard to the illustration.

While the invention has been described with respect to a limited number of embodiments, it will be appreciated that many variations, modifications and other applications of the invention may be made.

What is claimed is:

1. A system for treating lice and nits on a head of a patient, the system comprising:
    a cap for defining a treatment volume within said cap around the head of the patient;
    a container defining a storage volume, said storage volume containing a quantity of acetic acid at least partially adsorbed on a material comprising a large number of unbound miniscule porous particles;
    a housing defining a receptacle for receiving said container, said housing including a first puncturing element deployed for puncturing a first region of said container and a second puncturing element deployed for puncturing a second region of said container, said housing being in gas flow connection with the treatment volume within said cap; and
    a gas flow generator deployed for generating a flow of gas passing through said container and to the treatment volume within said cap,
    wherein said container is configured such that said flow of gas vaporizes said acetic acid so that said acetic acid is delivered into the treatment volume as a vapor without liquid.

2. The system of claim 1, wherein said housing comprises a first portion having said first puncturing element and a second portion having said second puncturing element, said first portion and said second portion being separable for insertion of said container, said first portion and said second portion being configured such that, after insertion of said container, bringing together of said first and second portions causes puncturing of said first and second regions of said container by said first and second puncturing elements.

3. The system of claim 2, wherein said first portion and said second portion are configured for threaded engagement such that, after insertion of said container, tightening of said threaded engagement causes puncturing of said first and second regions of said container by said first and second puncturing elements.

4. The system of claim 1, wherein said container further comprises at least one layer of filter material deployed such that, after puncturing of said first region of said container, said particulate solid material is retained within said container by said at least one layer of filter material.

5. The system of claim 1, wherein said container further comprises a filter compartment comprising at least one layer of filter material deployed such that, after puncturing of said first and second regions of said container, said particulate solid material is retained within said filter compartment.

6. The system of claim 1, wherein said cap further comprises a distributor having an inlet for receiving said flow of gas and at least two outlets for distributing said flow of gas within the treatment volume.

7. A method for treating lice and nits on a head of a patient, the method comprising the steps of:
    providing a system comprising:
        a cap for defining a treatment volume within said cap around the head of the patient,
        a container defining a storage volume, said storage volume containing
        a quantity of acetic acid at least partially adsorbed on a material comprising a large number of unbound miniscule porous particles,
        a housing defining a receptacle for receiving said container, said housing including a first puncturing element deployed for puncturing a first region of said container and a second puncturing element deployed for puncturing a second region of said container, said housing being in gas flow connection with the treatment volume within said cap, and
        a gas flow generator deployed for generating a flow of gas passing through said container and to the treatment volume within said cap;
    positioning the cap on the head of the patient to enclose a treatment volume;
    inserting the container into the housing and causing the first and second puncturing elements to puncture the first and second regions of the container; and
    actuating the gas circulator to generate a gas flow through the container and deliver gas with acetic acid vapor into the treatment volume, wherein said container is configured such that said gas flow vaporizes said acetic acid so that said acetic acid is delivered into the treatment volume as a vapor without liquid.

\* \* \* \* \*